US012195789B2

(12) United States Patent
Lee et al.

(10) Patent No.: US 12,195,789 B2
(45) Date of Patent: Jan. 14, 2025

(54) HIGHLY STABLE AND SPECIFIC MOLECULAR BEACONS ENCAPSULATED IN CATIONIC LIPOPLEX NANOPARTICLES AND APPLICATION THEREOF

(71) Applicant: Spot Biosystems Ltd., Palo Alto, CA (US)

(72) Inventors: Ly James Lee, Columbus, OH (US); Jiaming Hu, Arcadia, CA (US); Kwang Joo Kwak, Dublin, OH (US)

(73) Assignee: SPOT BIOSYSTEMS LTD., Palo Alto, CA (US)

( * ) Notice: Subject to any disclaimer, the term of this patent is extended or adjusted under 35 U.S.C. 154(b) by 93 days.

(21) Appl. No.: 17/357,862

(22) Filed: Jun. 24, 2021

(65) Prior Publication Data
US 2021/0332423 A1    Oct. 28, 2021

Related U.S. Application Data

(63) Continuation of application No. 15/880,309, filed on Jan. 25, 2018, now Pat. No. 11,085,071.

(60) Provisional application No. 62/499,652, filed on Feb. 1, 2017.

(51) Int. Cl.
*C12Q 1/6827* (2018.01)
*C12Q 1/6818* (2018.01)
*C12Q 1/6886* (2018.01)

(52) U.S. Cl.
CPC ......... *C12Q 1/6827* (2013.01); *C12Q 1/6818* (2013.01); *C12Q 1/6886* (2013.01); *C12N 2310/141* (2013.01); *C12N 2310/3517* (2013.01); *C12N 2310/531* (2013.01); *C12Q 2561/12* (2013.01); *C12Q 2600/112* (2013.01); *C12Q 2600/118* (2013.01); *C12Q 2600/156* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 9,217,151 B2 | 12/2015 | Yin et al. | |
| 9,541,480 B2 | 1/2017 | Chang et al. | |
| 2004/0112529 A1 | 6/2004 | Karlsson et al. | |
| 2011/0059867 A1 | 3/2011 | Kim et al. | |
| 2014/0094383 A1 | 4/2014 | Lee et al. | |
| 2014/0134263 A1 | 5/2014 | Wu | |
| 2014/0147846 A1* | 5/2014 | Wangh | C12Q 1/686 435/6.11 |
| 2015/0133319 A1* | 5/2015 | Fu | C12N 15/1065 506/4 |
| 2015/0191709 A1 | 7/2015 | Heron et al. | |
| 2015/0218651 A1 | 8/2015 | Lyden et al. | |
| 2016/0376639 A1* | 12/2016 | Vallabhaneni | C12Q 1/6818 506/9 |
| 2017/0275677 A1 | 9/2017 | Medintz et al. | |

FOREIGN PATENT DOCUMENTS

| CN | 101835903 A | 9/2010 |
|---|---|---|
| CN | 102242211 A | 11/2011 |
| CN | 103197066 B | 12/2015 |

OTHER PUBLICATIONS

Hu et al., Overhang molecular beacons encapsulated in tethered cationic lipoplex nanoparticles for detection of single-point mutation in extracellular vesicle-associated RNAs. Biomaterials 183:20-29 (2018).
Kwak et al., Formation and finite element analysis of tethered bilayer lipid structures. Langmuir. 26(23):18199-18208 (2010). [Abstract only].
Logozzi, et al. High levels of exosomes expressing CD63 and caveolin-1 in plasma of melanoma patients. PLoS One. 2009;4(4):e5219. (10 pages).
Massey et al., Time-Resolved Nucleic Acid Hybridization Beacons Utilizing Unimolecular and Toehold-Mediated Strand Displacement Designs. Analytical Chemistry. 87(23):11923-11931 (2015).
Okamoto. ECHO probes: a concept of fluorescence control for practical nucleic acid sensing. Chem. Soc. Rev. 40:5815-5828 (2011).
Real-time PCR Goes Prime Time. ThermoFisher Scientific. Retrieved from Internet URL: https://www.thermofisher.com/us/en/home/references/ambion-tech-support/rtpcr-analysis/tech-notes/rea . . . on Oct. 11, 2019.
Shi et al., DNA Molecular Beacon-Based Plastic Biochip: A Versatile and Sensitive Scanometric Detection Platform. ACS Appl. Mater. Interfaces 6(24): 21788-21797 (2014).
Tapp et al. Homogeneous scoring of single-nucleotide polymorphisms: comparison of the 5'—nuclease TaqMan assay and Molecular Beacon probes. Biotechniques 28(4):732-738 (2000).
Tauro et al., Comparison of ultracentrifugation, density gradient separation, and immunoaffinity capture methods for isolating human colon cancer cell line LIM1863-derived exosomes. Methods. 56(2):293-304 (2012).

(Continued)

*Primary Examiner* — Katherine D Salmon
(74) *Attorney, Agent, or Firm* — Wilson Sonsini Goodrich & Rosati

(57) ABSTRACT

The present invention discloses a method of detecting the presence of mutated genes, mRNAs or microRNAs in a subject. The method comprises the following steps: (1) Provide a body fluid sample containing cells, circulating tumor cells (CTCs), and/or extracellular vesicles (EVs); and use an analyzer having overhang molecular beacons to measure fluorescence signals generated by interactions between the body fluid sample and the overhang molecular beacons, so as to detect the presence of the mutated genes, mRNAs or microRNA. Furthermore, a biochip comprising a gold coating substrate and tethered lipoplex nanoparticles encapsulating the overhang molecular beacons is also provided in the invention.

13 Claims, 50 Drawing Sheets

Specification includes a Sequence Listing.

(56) References Cited

OTHER PUBLICATIONS

Tyagi, Sanjay, et al., Molecular Beacons: Probes that Fluoresce upon Hybridization. Nature Biotechnology 14(3):303-308 (1996).
U.S. Appl. No. 15/880,309 Final Office Action dat4ed Feb. 25, 2021.
U.S. Appl. No. 15/880,309 Non-Final Office Action dated Oct. 1, 2020.
U.S. Appl. No. 14/992,169 Office Action Dated Dec. 26, 2018.
U.S. Appl. No. 14/992,169 Office Action dated Jul. 10, 2017.
U.S. Appl. No. 14/992,169 Office Action dated Sep. 26, 2019.
U.S. Appl. No. 14/992,169 Office Action dated Jan. 10, 2018.
U.S. Appl. No. 15/880,309 Final Office Action dated Dec. 16, 2019.
U.S. Appl. No. 15/880,309 Office Action dated May 16, 2019.
Wu et al., Detection of extracellular RNAs in cancer and viral infection via tethered cationic lipoplex nanoparticles containing molecular beacons. Analytical Chemistry. 85(23):11265-11274 (2013).
Yin et al., Programming biomolecular self-assembly pathways. Nature. 451(7176): 318-322 (2008).

* cited by examiner

SEQUENCE LISTING

```
<160> NUMBER OF SEQ ID NOS: 14

<210> SEQ ID NO 1
<211> LENGTH: 37
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (11)..(11)
<223> OTHER INFORMATION: Locked nucleic acid (LNA)
<220> FEATURE:
<221> NAME/KEY: modified_base
<222> LOCATION: (14)..(14)
<223> OTHER INFORMATION: Locked nucleic acid (LNA)
<220> FEATURE:
<221> NAME/KEY: modified_base
<222> LOCATION: (17)..(17)
<223> OTHER INFORMATION: Locked nucleic acid (LNA)
<220> FEATURE:
<221> NAME/KEY: modified_base
<222> LOCATION: (20)..(20)
<223> OTHER INFORMATION: Locked nucleic acid (LNA)
<220> FEATURE:
<221> NAME/KEY: modified_base
<222> LOCATION: (23)..(23)
<223> OTHER INFORMATION: Locked nucleic acid (LNA)
<220> FEATURE:
<221> NAME/KEY: modified_base
<222> LOCATION: (26)..(26)
<223> OTHER INFORMATION: Locked nucleic acid (LNA)

<400> SEQUENCE: 1
cgcgatctca acatcagtct ctataagcta gatcgcg                              37

<210> SEQ ID NO 2
<211> LENGTH: 36
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (1)..(1)
<223> OTHER INFORMATION: Locked nucleic acid (LNA)
<220> FEATURE:
<221> NAME/KEY: modified_base
<222> LOCATION: (4)..(4)
<223> OTHER INFORMATION: Locked nucleic acid (LNA)
<220> FEATURE:
<221> NAME/KEY: modified_base
<222> LOCATION: (7)..(7)
<223> OTHER INFORMATION: Locked nucleic acid (LNA)
```

```
<220> FEATURE:
<221> NAME/KEY: modified_base
<222> LOCATION: (10)..(10)
<223> OTHER INFORMATION: Locked nucleic acid (LNA)
<220> FEATURE:
<221> NAME/KEY: modified_base
<222> LOCATION: (13)..(13)
<223> OTHER INFORMATION: Locked nucleic acid (LNA)
<220> FEATURE:
<221> NAME/KEY: modified_base
<222> LOCATION: (16)..(16)
<223> OTHER INFORMATION: Locked nucleic acid (LNA)
<220> FEATURE:
<221> NAME/KEY: modified_base
<222> LOCATION: (19)..(19)
<223> OTHER INFORMATION: Locked nucleic acid (LNA)
<220> FEATURE:
<221> NAME/KEY: modified_base
<222> LOCATION: (22)..(22)
<223> OTHER INFORMATION: Locked nucleic acid (LNA)

<400> SEQUENCE: 2
tcaacatcag tctgataagc tagattatca gactga                                36

<210> SEQ ID NO 3
<211> LENGTH: 35
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (3)..(3)
<223> OTHER INFORMATION: Locked nucleic acid (LNA)
<220> FEATURE:
<221> NAME/KEY: modified_base
<222> LOCATION: (6)..(6)
<223> OTHER INFORMATION: Locked nucleic acid (LNA)
<220> FEATURE:
<221> NAME/KEY: modified_base
<222> LOCATION: (9)..(9)
<223> OTHER INFORMATION: Locked nucleic acid (LNA)
<220> FEATURE:
<221> NAME/KEY: modified_base
<222> LOCATION: (12)..(12)
<223> OTHER INFORMATION: Locked nucleic acid (LNA)
<220> FEATURE:
<221> NAME/KEY: modified_base
<222> LOCATION: (15)..(15)
<223> OTHER INFORMATION: Locked nucleic acid (LNA)
<220> FEATURE:
<221> NAME/KEY: modified_base
<222> LOCATION: (18)..(18)
<223> OTHER INFORMATION: Locked nucleic acid (LNA)
<220> FEATURE:
<221> NAME/KEY: modified_base
<222> LOCATION: (21)..(21)
<223> OTHER INFORMATION: Locked nucleic acid (LNA)

<400> SEQUENCE: 3
cctacgccac cagctccaac taatggagct ggtgg                                 35

<210> SEQ ID NO 4
<211> LENGTH: 35
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (3)..(3)
<223> OTHER INFORMATION: Locked nucleic acid (LNA)
<220> FEATURE:
<221> NAME/KEY: modified_base
<222> LOCATION: (6)..(6)
```

<223> OTHER INFORMATION: Locked nucleic acid (LNA)
<220> FEATURE:
<221> NAME/KEY: modified_base
<222> LOCATION: (9)..(9)
<223> OTHER INFORMATION: Locked nucleic acid (LNA)
<220> FEATURE:
<221> NAME/KEY: modified_base
<222> LOCATION: (12)..(12)
<223> OTHER INFORMATION: Locked nucleic acid (LNA)
<220> FEATURE:
<221> NAME/KEY: modified_base
<222> LOCATION: (15)..(15)
<223> OTHER INFORMATION: Locked nucleic acid (LNA)
<220> FEATURE:
<221> NAME/KEY: modified_base
<222> LOCATION: (18)..(18)
<223> OTHER INFORMATION: Locked nucleic acid (LNA)
<220> FEATURE:
<221> NAME/KEY: modified_base
<222> LOCATION: (21)..(21)
<223> OTHER INFORMATION: Locked nucleic acid (LNA)

<400> SEQUENCE: 4
cgccacaagc tccaactacc acttagttgg agctt                                    35

<210> SEQ ID NO 5
<211> LENGTH: 36
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (3)..(3)
<223> OTHER INFORMATION: Locked nucleic acid (LNA)
<220> FEATURE:
<221> NAME/KEY: modified_base
<222> LOCATION: (6)..(6)
<223> OTHER INFORMATION: Locked nucleic acid (LNA)
<220> FEATURE:
<221> NAME/KEY: modified_base
<222> LOCATION: (9)..(9)
<223> OTHER INFORMATION: Locked nucleic acid (LNA)
<220> FEATURE:
<221> NAME/KEY: modified_base
<222> LOCATION: (12)..(12)
<223> OTHER INFORMATION: Locked nucleic acid (LNA)
<220> FEATURE:
<221> NAME/KEY: modified_base
<222> LOCATION: (15)..(15)
<223> OTHER INFORMATION: Locked nucleic acid (LNA)
<220> FEATURE:
<221> NAME/KEY: modified_base
<222> LOCATION: (18)..(18)
<223> OTHER INFORMATION: Locked nucleic acid (LNA)
<220> FEATURE:
<221> NAME/KEY: modified_base
<222> LOCATION: (21)..(21)
<223> OTHER INFORMATION: Locked nucleic acid (LNA)

<400> SEQUENCE: 5
acgccatcag ctccaactac cacgagttgg agctga                                   36

<210> SEQ ID NO 6
<211> LENGTH: 35
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (3)..(3)
<223> OTHER INFORMATION: Locked nucleic acid (LNA)
<220> FEATURE:
<221> NAME/KEY: modified_base

```
<222> LOCATION: (6)..(6)
<223> OTHER INFORMATION: Locked nucleic acid (LNA)
<220> FEATURE:
<221> NAME/KEY: modified_base
<222> LOCATION: (9)..(9)
<223> OTHER INFORMATION: Locked nucleic acid (LNA)
<220> FEATURE:
<221> NAME/KEY: modified_base
<222> LOCATION: (12)..(12)
<223> OTHER INFORMATION: Locked nucleic acid (LNA)
<220> FEATURE:
<221> NAME/KEY: modified_base
<222> LOCATION: (15)..(15)
<223> OTHER INFORMATION: Locked nucleic acid (LNA)
<220> FEATURE:
<221> NAME/KEY: modified_base
<222> LOCATION: (18)..(18)
<223> OTHER INFORMATION: Locked nucleic acid (LNA)
<220> FEATURE:
<221> NAME/KEY: modified_base
<222> LOCATION: (21)..(21)
<223> OTHER INFORMATION: Locked nucleic acid (LNA)

<400> SEQUENCE: 6
acgccaacag ctccaactac cagagttgga gctgt                              35

<210> SEQ ID NO 7
<211> LENGTH: 36
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (1)..(1)
<223> OTHER INFORMATION: Locked nucleic acid (LNA)
<220> FEATURE:
<221> NAME/KEY: modified_base
<222> LOCATION: (4)..(4)
<223> OTHER INFORMATION: Locked nucleic acid (LNA)
<220> FEATURE:
<221> NAME/KEY: modified_base
<222> LOCATION: (6)..(6)
<223> OTHER INFORMATION: Labelled with the chromophore iCy3
<220> FEATURE:
<221> NAME/KEY: modified_base
<222> LOCATION: (7)..(7)
<223> OTHER INFORMATION: Locked nucleic acid (LNA)
<220> FEATURE:
<221> NAME/KEY: modified_base
<222> LOCATION: (10)..(10)
<223> OTHER INFORMATION: Locked nucleic acid (LNA)
<220> FEATURE:
<221> NAME/KEY: modified_base
<222> LOCATION: (13)..(13)
<223> OTHER INFORMATION: Locked nucleic acid (LNA)
<220> FEATURE:
<221> NAME/KEY: modified_base
<222> LOCATION: (16)..(16)
<223> OTHER INFORMATION: Locked nucleic acid (LNA)

<400> SEQUENCE: 7
agctgcatga tgagctgcac ggtggcagct catcat                             36

<210> SEQ ID NO 8
<211> LENGTH: 36
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (1)..(1)
<223> OTHER INFORMATION: Locked nucleic acid (LNA)
<220> FEATURE:
```

```
<221> NAME/KEY: modified_base
<222> LOCATION: (4)..(4)
<223> OTHER INFORMATION: Locked nucleic acid (LNA)
<220> FEATURE:
<221> NAME/KEY: modified_base
<222> LOCATION: (6)..(6)
<223> OTHER INFORMATION: Labelled with the chromophore iCy3
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (10)..(10)
<223> OTHER INFORMATION: Locked nucleic acid
<220> FEATURE:
<221> NAME/KEY: modified_base
<222> LOCATION: (13)..(13)
<223> OTHER INFORMATION: Locked nucleic acid
<220> FEATURE:
<221> NAME/KEY: modified_base
<222> LOCATION: (16)..(16)
<223> OTHER INFORMATION: Locked nucleic acid

<400> SEQUENCE: 8
agctgcgtga tgagctgcac ggtggcagct catcac                                 36

<210> SEQ ID NO 9
<211> LENGTH: 36
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (1)..(1)
<223> OTHER INFORMATION: Locked nucleic acid (LNA)
<220> FEATURE:
<221> NAME/KEY: modified_base
<222> LOCATION: (4)..(4)
<223> OTHER INFORMATION: Locked nucleic acid (LNA)
<220> FEATURE:
<221> NAME/KEY: modified_base
<222> LOCATION: (6)..(6)
<223> OTHER INFORMATION: Labelled with the chromophore iCy3
<220> FEATURE:
<221> NAME/KEY: modified_base
<222> LOCATION: (7)..(7)
<223> OTHER INFORMATION: Locked nucleic acid (LNA)
<220> FEATURE:
<221> NAME/KEY: modified_base
<222> LOCATION: (10)..(10)
<223> OTHER INFORMATION: Locked nucleic acid (LNA)
<220> FEATURE:
<221> NAME/KEY: modified_base
<222> LOCATION: (13)..(13)
<223> OTHER INFORMATION: Locked nucleic acid (LNA)
<220> FEATURE:
<221> NAME/KEY: modified_base
<222> LOCATION: (16)..(16)
<223> OTHER INFORMATION: Locked nucleic acid (LNA)

<400> SEQUENCE: 9
ttggcccgcc caaaatctgt gattagattt tgggcg                                 36

<210> SEQ ID NO 10
<211> LENGTH: 36
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (1)..(1)
<223> OTHER INFORMATION: Locked nucleic acid
```

<220> FEATURE:
<221> NAME/KEY: modified_base
<222> LOCATION: (4)..(4)
<223> OTHER INFORMATION: Locked nucleic acid (LNA)
<220> FEATURE:
<221> NAME/KEY: modified_base
<222> LOCATION: (6)..(6)
<223> OTHER INFORMATION: Labelled with the chromophore iCy3
<220> FEATURE:
<221> NAME/KEY: modified_base
<222> LOCATION: (7)..(7)
<223> OTHER INFORMATION: Locked nucleic acid (LNA)
<220> FEATURE:
<221> NAME/KEY: modified_base
<222> LOCATION: (10)..(10)
<223> OTHER INFORMATION: Locked nucleic acid (LNA)
<220> FEATURE:
<221> NAME/KEY: modified_base
<222> LOCATION: (13)..(13)
<223> OTHER INFORMATION: Locked nucleic acid (LNA)
<220> FEATURE:
<221> NAME/KEY: modified_base
<222> LOCATION: (16)..(16)
<223> OTHER INFORMATION: Locked nucleic acid (LNA)

<400> SEQUENCE: 10
ttggccagcc caaaatctgt gattagattt tgggct                                    36

<210> SEQ ID NO 11
<211> LENGTH: 36
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (1)..(1)
<223> OTHER INFORMATION: Locked nucleic acid (LNA)
<220> FEATURE:
<221> NAME/KEY: modified_base
<222> LOCATION: (4)..(4)
<223> OTHER INFORMATION: Locked nucleic acid (LNA)
<220> FEATURE:
<221> NAME/KEY: modified_base
<222> LOCATION: (6)..(6)
<223> OTHER INFORMATION: Labelled with the chromophore iCy3
<220> FEATURE:
<221> NAME/KEY: modified_base
<222> LOCATION: (7)..(7)
<223> OTHER INFORMATION: Locked nucleic acid (LNA)
<220> FEATURE:
<221> NAME/KEY: modified_base
<222> LOCATION: (10)..(10)
<223> OTHER INFORMATION: Locked nucleic acid (LNA)
<220> FEATURE:
<221> NAME/KEY: modified_base
<222> LOCATION: (13)..(13)
<223> OTHER INFORMATION: Locked nucleic acid (LNA)
<220> FEATURE:
<221> NAME/KEY: modified_base
<222> LOCATION: (16)..(16)
<223> OTHER INFORMATION: Locked nucleic acid (LNA)

<400> SEQUENCE: 11
gtacacttta ggtcctttcc caggaaagga cctaaa                                    36

<210> SEQ ID NO 12
<211> LENGTH: 36
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (1)..(1)

```
<223> OTHER INFORMATION: Locked nucleic acid (LNA)
<220> FEATURE:
<221> NAME/KEY: modified_base
<222> LOCATION: (4)..(4)
<223> OTHER INFORMATION: Locked nucleic acid (LNA)
<220> FEATURE:
<221> NAME/KEY: modified_base
<222> LOCATION: (6)..(6)
<223> OTHER INFORMATION: Labelled with the chromophore iCy3
<220> FEATURE:
<221> NAME/KEY: modified_base
<222> LOCATION: (7)..(7)
<223> OTHER INFORMATION: Locked nucleic acid (LNA)
<220> FEATURE:
<221> NAME/KEY: modified_base
<222> LOCATION: (10)..(10)
<223> OTHER INFORMATION: Locked nucleic acid (LNA)
<220> FEATURE:
<221> NAME/KEY: modified_base
<222> LOCATION: (13)..(13)
<223> OTHER INFORMATION: Locked nucleic acid (LNA)
<220> FEATURE:
<221> NAME/KEY: modified_base
<222> LOCATION: (16)..(16)
<223> OTHER INFORMATION: Locked nucleic acid (LNA)

<400> SEQUENCE: 12
gtacacttgg ttgatgatga catcatcatc aaccaa                                    36

<210> SEQ ID NO 13
<211> LENGTH: 30
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (18)..(18)
<223> OTHER INFORMATION: Locked nucleic acid (LNA)
<220> FEATURE:
<221> NAME/KEY: modified_base
<222> LOCATION: (21)..(21)
<223> OTHER INFORMATION: Locked nucleic acid (LNA)
<220> FEATURE:
<221> NAME/KEY: modified_base
<222> LOCATION: (24)..(24)
<223> OTHER INFORMATION: Locked nucleic acid (LNA)
<220> FEATURE:
<221> NAME/KEY: modified_base
<222> LOCATION: (26)..(26)
<223> OTHER INFORMATION: Locked nucleic acid (LNA)
<220> FEATURE:
<221> NAME/KEY: modified_base
<222> LOCATION: (28)..(28)
<223> OTHER INFORMATION: Locked nucleic acid (LNA)
<220> FEATURE:
<221> NAME/KEY: modified_base
<222> LOCATION: (30)..(30)
<223> OTHER INFORMATION: Locked nucleic acid (LNA)

<400> SEQUENCE: 13
gaccgtatag taatgctata cggtccacta                                           30

<210> SEQ ID NO 14
<211> LENGTH: 30
<212> TYPE: DNA
<213> ORGANISM: Artificial Sequence
<220> FEATURE:
<223> OTHER INFORMATION: Synthetic molecular beacon
<220> FEATURE:
<221> NAME/KEY: modified_base
<222> LOCATION: (18)..(18)
<223> OTHER INFORMATION: Locked nucleic acid
<220> FEATURE:
<221> NAME/KEY: modified_base
```

```
<222> LOCATION: (21)..(21)
<223> OTHER INFORMATION: Locked nucleic acid
<220> FEATURE:
<221> NAME/KEY: modified_base
<222> LOCATION: (24)..(24)
<223> OTHER INFORMATION: Locked nucleic acid
<220> FEATURE:
<221> NAME/KEY: modified_base
<222> LOCATION: (26)..(26)
<223> OTHER INFORMATION: Locked nucleic acid
<220> FEATURE:
<221> NAME/KEY: modified_base
<222> LOCATION: (28)..(28)
<223> OTHER INFORMATION: Locked nucleic acid
<220> FEATURE:
<221> NAME/KEY: modified_base
<222> LOCATION: (30)..(30)
<223> OTHER INFORMATION: Locked nucleic acid

<400> SEQUENCE: 14
gaccgtatag taatgctata cggtctacta                                  30
```

HIGHLY STABLE AND SPECIFIC MOLECULAR BEACONS ENCAPSULATED IN CATIONIC LIPOPLEX NANOPARTICLES AND APPLICATION THEREOF

CROSS REFERENCE

This Application is a continuation of U.S. patent application Ser. No. 15/880,309, filed Jan. 25, 2018, now U.S. Pat. No. 11,085,071, issued Aug. 10, 2021, which claims the benefit of U.S. Provisional Application No. 62/499,652, filed on Feb. 1, 2017, which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jan. 20, 2018, is named 54841_702_301.txt and is 11,000 bytes in size.

TECHNICAL FIELD OF THE INVENTION

The present invention relates to a method of detecting the presence of mutated genes, mRNAs or microRNAs in a subject by using highly stable and specific molecular beacons encapsulated in lipoplex nanoparticles. In particular, the highly stable and specific molecular beacons are polynucleotides and comprise an overhang section and applied for detection of a single point mutation of genes, mRNAs or microRNAs.

BACKGROUND OF THE INVENTION

Early and convenient detection has become extremely important against various diseases including cancer, cardiovascular diseases and infectious diseases. The earlier a disease is diagnosed, the more likely it can be cured or successfully managed. Although significant progress has been made in disease diagnosis and treatment, mortality rates of diseases such as cancer, heart failure and AIDS have not changed much in the last several decades. One reason is the lack of sensitive, easy, fast, non-invasive and affordable screening tests for early disease detection. 'Liquid biopsy' by capturing and identifying circulating cancer cells (CTCs) and extracellular vesicles (EVs) in human blood or body fluid samples, such as urine, saliva, amniotic fluid and breast milk, has gained a great deal of interest in recent years because of its potential for early and patient-friendly disease detection and monitoring.

After the CTC or EV separation/isolation process, the DNA and RNA content in the isolated CTCs or EVs needs to be collected, and methods, such as next generation sequencing (NGS), DNA/RNA microarrays, polymerase chain reaction (PCR), are needed to identify surface antigens on CTCs or EVs and DNA/RNA/protein targets inside the isolated CTCs or EVs. The entire sample preparation and target detection process requires more than 30 steps, so it is time consuming, expensive and labor intensive. Furthermore, the separation/isolation and identification/amplification methods are based on the total nucleic acids and proteins collected from all CTCs or EVs secreted from normal and disease cells. Since EVs secreted from both normal and disease cells may contain similar biomolecules and EVs from disease cells are a minority, particularly in the early stage of the disease, these methods cannot provide high detection sensitivity. New detection methods are needed that can simultaneously identify intra-EV RNA targets.

US 20140094383 has disclosed a biochip with tethered cationic lipoplex nanoparticles (CLNs) where intra-vesicular RNAs are detected by the fusion of negatively charged EVs with positively charged lipoplex nanoparticles tethered on the biochip surface by electrostatic interactions. However, the current conventional molecular beacon (Co-MB) design cannot distinguish less than two mutations of target RNAs without generating strong false positive signals. This greatly limits the value of the CLN technology. Furthermore, the Co-MB is not stable in solution and in CLNs. It needs to be prepared fresh and used in the biochip within a few hours, which is not suitable for large scale clinic use.

Since cancer is a genetic disease caused by the accumulation of mutations and chromosomal aberrations. Mutations and depletion/fusion in oncogenes and tumor suppressor genes determine the phenotype of a tumor: its location, aggressiveness, and sensitivity to therapeutics. Increasingly, somatic mutations and depletion/fusion have been proposed as biomarkers for cancer prognosis and prediction of therapeutic efficacy. Recent examples include the prediction of response or resistance to certain oncology drugs based on mutations in EGFR or KRAS gene, and ALK gene depletion/fusion.

A widely used strategy for detecting single mutations is qRT-PCR in which one or both primers are designed to anneal at sites of sequence variation. Ideally, a primer whose sequence matches a specific variant should selectively amplify only that variant. However, in practice, significant mismatched amplification occurs.

Based on the aforementioned description, it is vital to develop an accurate and specific technology for detecting the presence of mutated genes, mRNAs or microRNAs in a subject.

SUMMARY OF THE INVENTION

In one aspect, the present invention discloses a method of detecting the presence of mutated genes, mRNAs or microRNAs in a subject, The method comprises the following steps. (1) Provide a body fluid sample containing cells, circulating tumor cells (CTCs), and/or extracellular vesicles (EVs); and (2) Use an analyzer having overhang molecular beacons (Oh-MBs) to measure fluorescence signals generated by interactions between the body fluid sample and the overhang molecular beacons, so as to detect the presence of the mutated genes, mRNAs or microRNAs. The overhang molecular beacons comprise or consist of a stem having at least 9-base pairs, a loop having at least 4 bases, an overhang section of at least 5 complementary bases to the mutated genes, mRNAs or microRNAs at the end of the stem, a fluorescence dye and a quencher at the 3' end; and where the last complementary base of the overhang section or the first complementary base of the stem in the overhang molecular beacons is corresponding to a single-point mutated base of the mutated genes, mRNAs or microRNAs.

In general, the Oh-MBs encapsulated within lipoplex nanoparticles, such as cationic lipoplex nanoparticles (CLNs) used in CLN biochips, can precisely distinguish the wild-type nucleotide sequence and mutant bases because the designed structure will stop the hybridization reaction between MB sequence and wild-type/mutant sequences. The Oh-MBs can also detect depleted/fused mRNAs in EVs.

Furthermore, the lipoplex nanoparticles containing specially designed overhang molecular beacons (Oh-MBs) in biochips are able to capture and characterize circular tumor cells (CTCs) and extracellular vesicles (EVs) in blood and other body fluids sample based on intra-vesicular RNA targets, particularly single-point gene mutations and gene depletion/fusion in cancer. Theses Oh-MBs containing CLNs can also be used to capture and identify viruses and other pathogens. Utilize the aforementioned design concept, fusion of Oh-MBs-containing lipoplex nanoparticles allows direct detection of cellular nucleic acids and intra-vesicular nucleic acids contained inside the captured EVs, viruses and other pathogens without any amplification steps.

In another aspect, the present invention provides a biochip for detecting mutated genes, mRNAs or microRNAs. The biochips comprises a gold coating substrate and lipoplex nanoparticles. The lipoplex nanoparticles tether on the gold coating substrate and encapsulate a plaurity of overhang molecular beacons (Oh-MBs). The overhang molecular beacons comprise or consist of a stem having at least 9-base pairs, a loop having at least 4 bases, an overhang section of at least 5 complementary bases to the mutated genes, mRNAs or microRNAs at the end of the stem, a fluorescence dye and a quencher at the 3' end; and where the last complementary base of the overhang section or the first complementary base of the stem in the overhang molecular beacons is corresponding to a single-point mutated base of the mutated gene, mRNAs, or microRNAs.

Typically, one of the Oh-MBs has the 12-base pairs stem, the 6-base or nucleotide loop and the overhang section of 6 complementary bases to target RNAs added at the end of the stem. The free energy $\Delta G$ of the Oh-MB is $-10.31$ kcal/mol at 37° C. This 12-base pairs stem is much more stable in the cationic lipoplex nanoparticle based on its lower free energy. The 6-base or nucleotide loop is less likely to be denatured because of its more compact structure comparing to the traditional molecular beacons (Co-MB). The 6-base overhang section also causes the 12-base stem strand to be quickly replaced by hybridizing with target RNA strand because of its high reaction rate constant ($10^6$-$10^7$ $M^{-1}$ $s^{-1}$).

In accordance with the present invention, the aforementioned method of detecting the presence of mutated genes, mRNAs or microRNAs in a subject is achieved by using the novel and unique overhang molecular beacons (Oh-MBs). Moreover, the overhang molecular beacons are encapsulated within the lipoplex nanoparticles and then perform lyophilization process to obtain the dry powder of lipoplex nanoparticles encapsulated Oh-MBs. Moreover, the lipoplex nanoparticles encapsulated Oh-MBs are able to bind or tether to a substrate through any physical or chemical interactions, or to be added to fuse with antibodies-captured EVs or cells to form the invented biochips for detecting mutated genes, mRNAs or microRNAs.

BRIEF DESCRIPTION OF THE DRAWING

FIG. 1A shows illustration of CLN-TIRF technology; FIG. 1B is Schematic illustration of Oh-MB for signal gain of target RNA in CLN-EV complex; FIG. 1C is Structure of Co-MB and Oh-MB; FIG. 1D is TIRF images of timeline comparison of CLN-Co-MB and CLN-Oh-MB incubated in PBS at 37° C., and FIG. 1E is Linear scale comparison of CLN-Co-MB and CLN-Oh-MB (FAM is fluorescein, BHQ is a dark quencher);

FIG. 2A is Representative TIRF images of miR-21_oligo expression in varied concentrations of SVs (0, 1.2%, 2.5%, 5%, 10%, 20% and 40%) detected by using CLN-Co-MB (top row) or CLN-Oh-MB (2nd row); FIG. 2B is Fluorescence calibration curves of miR-21_oligo expression in SVs using CLN-Co-MB or CLN-Oh-MB individually vs percentage of SV;

FIG. 2C is Linear scale comparison of limit of detection (LOD) between CLN-Oh-MB and CLN-Co-MB; FIG. 2D is Fluorescence intensity enhancement of CLN-Oh-MB relative to CLN-Co-MB at varied concentrations of SVs; FIG. 2E is Stability of recovery test of fresh and lyophilized CLN-Co-MB and CLN-Oh-MB; FIG. 2F is Signal recovery test of fresh and lyophilized CLN-Co-MB and CLN-Oh-MB.

FIGS. 3A and 3B are Representative live cell images of miR-21 in A549 and HBEC cell lines using CLN-Co-MB and CLN-Oh-MB, respectively (Inside upper left, zoomed phase contrast image of individual cells); FIG. 3C is Fluorescence intensity of A549 cells (red circles) and HBEC cells (black squares) treated with CLN-Co-MB or CLN-Oh-MB; FIG. 3D is Comparison of signal-to-background ratios of CLN-Co-MB and CLN-Oh-MB; FIG. 3E is Fluorescence enhancement of CLN-Oh-MB relative to CLN-Co-MB; FIG. 3F and FIG. 3G are Comparison of TIRF images of miR-21 expression in A549 (upper row) and HBEC EVs (bottom row) using CLN-Co-MB and CLN-Oh-MB, respectively; FIG. 3H is Fluorescence intensity of A549 (red circles) and HBEC EVs (black squares) with CLN-Co-MB and CLN-Oh-MB; FIG. 3I is Comparison of signal-to-background ratios of CLN-Co-MB and CLN-Oh-MB; FIG. 3J is EV-based fluorescence enhancement of CLN-Oh-MB relative to CLN-Co-MB;

FIG. 4A, FIG. 4E, FIG. 4B, and FIG. 4F are Linear scale comparison of wild type, 1-mismatch, 2-mismatch and 3-mismatch of miR-21_oligo detected by CLN-Co-MB and CLN-Oh-MB, respectively; FIG. 4C and FIG. 4D are Hybridization hypothesis of CLN-Co-MB and CLN-Oh-MB, respectively; FIG. 4G, FIG. 4H, FIG. 4I, and FIG. 4J are Comparison of TIRF images and linear scales of KRAS mutations detected by CLN-Oh-MB in exosomes collected from pancreatic cell lines (HUT78, PaCa-2, AsPC-1 and Panc03.27), respectively;

BRIEF DESCRIPTION OF THE SEQUENCE LISTING

Figure 1A:
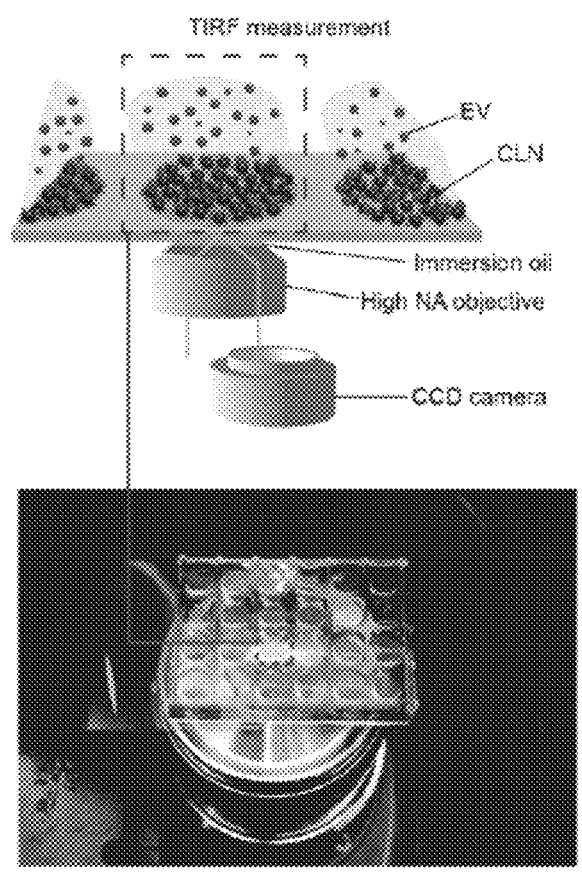
FIGS. 1A-1E show Principle of the CLN biochip.

In the following sequence listing, the symbol of [a], [c], [g], and [t] represent a modified base of locked nucleic acid (LNA) of a, c, g and t, respectively.

SEQ ID No 1 is a polynucleotide sequence of molecule beacon named Co-MB-miR21 set forth as follows:

```
                                          (SEQ ID No 1)
    cgcgatctca [a]ca[t]ca[g]tc[t] ct[a]taa[g]cta gatcgcg
```

The SEQ ID No 1 further has a fluorophore or chromophore at the 5' end and a quencher at the 3' end. Preferably, the fluorophore at the 5' end is 6FAM and the quencher at the 3'end is BHQ1.

SEQ ID No 2 is a polynucleotide sequence of the molecule beacon named Oh-MB-miR21 set forth as follows:

```
                                          (SEQ ID No 2)
    [t]ca[a]ca[t]ca[g] tc[t]ga[t]aa[g]c t[a]gattatca gactga
```

The SEQ ID No 2 further has a fluorophore or chromophore at the 5' end and a quencher at the 3' end. Preferably, the fluorophore at the 5' end is 6FAM and the quencher at the 3' end is BHQ1.

SEQ ID No 3 is a polynucleotide sequence of molecule beacon named Oh-MB-KRAS$^{WT}$ set forth as follows:

```
                                          (SEQ ID No 3)
    cc[t]ac[g]cc[a]c c[a]gc[t]cc[a]ac [t]aatggagct ggtgg
```

SEQ ID No 4 is a polynucleotide sequence of molecule beacon named Oh-MB-KRAS$^{G12C}$ set forth as follows:

```
                                          (SEQ ID No 4)
    cg[c]ca[c]aa[g]ct[c]ca[a]ct[a]cc [a]cttagttgg agctt
```

SEQ ID No 5 is a oligonucleotide sequence of molecule beacon named Oh-MB-KRAS$^{G12D}$ set forth as follows:

```
                                          (SEQ ID No 5)
    ac[g]cc[a]tc[a]g c[t]cc[a]ac[t]ac [c]acgagttgg agctga
```

SEQ ID No 6 is oligonucleotide sequence of molecule beacon named Oh-MB-KRAS$^{G12V}$ set forth as follows:

```
                                          (SEQ ID No 6)
    ac[g]cc[a]ac[a]g c[t]cc[a]ac[t]ac [c]agagttgga gctgt
```

The SEQ ID No 3, 4, 5 or 6 further has a fluorophore at the 5' end and a quencher at the 3' end. Preferably, the fluorophore at the 5' end is 6FAM and the quencher at the 3' end is BHQ1.

SEQ ID No 7 is a polynucleotide sequence of molecule beacon named Ohi-MB-EGFR$^{Mut}$ (T790M) set forth as follows:

```
                                          (SEQ ID No 7)
    [a]gc[t]gc/iCy3/[a]tg[a] tg[a]gc[t]gcac ggtggcagct catcat
```

SEQ ID No 8 is a polynucleotide sequence of molecule beacon named Ohi-MB-EGFR$^{WT}$ (T790M) set forth as follows:

```
                                          (SEQ ID No 8)
    [a]gc[t]gc/iCy3/[g]tg[a] tg[a]gc[t]gcac ggtggcagct catcac
```

SEQ ID No 9 is a polynucleotide sequence of molecule beacon named Ohi-MB-EGFR$^{Mut}$ (L845R) set forth as follows:

```
                                          (SEQ ID No 9)
    [t]tg[g]cc/iCy3/[c]gc[c] ca[a]aa[t]ctgt gattagattt tgggcg
```

SEQ ID No 10 is a polynucleotide sequence of molecule beacon named Ohi-MB-EGFR$^{WT}$ (L858R) set forth as follows:

```
                                          (SEQ ID No 10)
    [t]tg[g]cc/iCy3/[a]gc[c] ca[a]aa[t]ctgt gattagattt tgggct
```

The SEQ ID No 7, 8. 9 or 10 further has a quencher at the 3' end. Preferably, the quencher at the 3' end is BHQ2.

SEQ ID No 11 is a polynucleotide sequence of molecule beacon named Ohi-MB-EML4-ALK v1 set forth as follows:

(SEQ ID No 11)
[g]ta[c]ac/iCy3/[t]tt[a] gg[t]cc[t]ttcc caggaaagga cctaaa

SEQ ID No 12 is a polynucleotide sequence of molecule beacon named Ohi-MB-EML4-ALK v3a set forth as follows:

(SEQ ID No 12)
[g]ta[c]ac/iCy3/[t]tg[g] tt[g]at[g]atga catcatcatc aaccaa

The SEQ ID No 11 or 12 further has a quencher at the 3' end. Preferably, the quencher at the 3' end is BHQ2.

SEQ ID No 13 is a polynucleotide sequence of molecule beacon named Oh-MB-411$^{ED}$ set forth as follows:

(SEQ ID No 13)
gaccgtatag taatgct[a]ta [c]gg[t]c[c]a[c]t[a]

SEQ ID No 14 is a polynucleotide sequence of molecule beacon named Oh-MB-411$^{WT\,(L}$858R) set forth as follows:

(SEQ ID No 14)
gaccgtatag taatgct[a]ta [c]gg[t]c[t]a[c]t[a]

The SEQ ID No 13 or 14 further has a fluorophore or chromophore at the 5' end and a quencher at the 3' end. Preferably, the fluorophore at the 5' end is 6FAM and quencher at the 3'end is BHQ1.

The aforementioned sequences are summed in TABLE 1

TABLE 1

| NAME | SEQ ID | SEQUENCE | COMMENT |
|---|---|---|---|
| Co-MB-miR21 | 1 | cgcgatctca [a]ca[t]ca[g]tc[t] ct[a]taa[g]cta gatcgcg | 6FAM at the 5' end<br>BHQ1 at the 3' end |
| Oh-MB-miR21 | 2 | [t]ca[a]ca[t]ca[g] tc[t]ga[t]aa[g]c t[a]gattatca gactga | 6FAM at the 5' end<br>BHQ1 at the 3' end |
| Oh-MB-KRAS$^{WT}$ | 3 | cc[t]ac[g]cc[a]c c[a]gc[t]cc[a]ac [t]aatggagct ggtgg | 6FAM at the 5' end<br>BHQ1 at the 3' end |
| Oh-MB-KRAS$^{G12C}$ | 4 | cg[c]ca[c]aa[g]c t[c]ca[a]ct[a]cc [a]cttagttgg agctt | 6FAM at the 5' end<br>BHQ1 at the 3' end |
| Oh-MB-KRAS$^{G12D}$ | 5 | ac[g]cc[a]tc[a]g c[t]cc[a]ac[t]ac [c]acgagttgg agctga | 6FAM at the 5' end<br>BHQ1 at the 3' end |
| Oh-MB-KRAS$^{G12V}$ | 6 | ac[g]cc[a]ac[a]g c[t]cc[a]ac[t]ac [c]agagttgga gctgt | 6FAM at the 5' end<br>BHQ1 at the 3' end |
| Ohi-MB-EGFR$^{Mut}$ (T790M) | 7 | [a]gc[t]gc/iCy3/[a]tg[a] tg[a]gc[t]gcac ggtggcagct catcat | BHQ2 at the 3' end |
| Ohi-MB-EGFR$^{WT}$ (T790M) | 8 | [a]gc[t]gc/iCy3/[g]tg[a] tg[a]gc[t]gcac ggtggcagct catcac | BHQ2 at the 3' end |
| Ohi-MB-EGFR$^{Mut}$ (L845R) | 9 | [t]tg[g]cc/iCy3/[c]gc[c] ca[a]aa[t]ctgt gattagattt tgggcg | BHQ2 at the 3' end |
| Ohi-MB-EGFR$^{WT}$ (L858R) | 10 | [t]tg[g]cc/iCy3/[a]gc[c] ca[a]aa[t]ctgt gattagattt tgggct | BHQ2 at the 3' end |
| Ohi-MB-EML4-ALK v1 | 11 | [g]ta[c]ac/iCy3/[t]tt[a] gg[t]cc[t]ttcc caggaaagga cctaaa | BHQ2 at the 3' end |
| Ohi-MB-EML4-ALK v3a | 12 | [g]ta[c]ac/iCy3/[t]tg[g] tt[g]at[g]atga catcatcatc aaccaa | BHQ2 at the 3' end |
| Oh-MB-411$^{ED}$ | 13 | gaccgtatag taatgct[a]ta [c]gg[t]c[c]a[c]t[a] | 6FAM at the 5' end<br>BHQ1 at the 3' end |
| Oh-MB-411$^{WT}$ | 14 | gaccgtatag taatgct[a]ta [c]gg[t]c[t]a[c]t[a] | 6FAM at the 5' end<br>BHQ1 at the 3' end |

In conclusion, the present invention relates to designs of lipoplex nanoparticles containing highly stable and specific molecular probes, such as overhang molecular beacons, for detection of RNA targets including single-point mutated and depleted/fused messenger RNAs, microRNAs, and long non-coding RNAs (lncRNA), in extracellular vesicles (EVs) and viruses using various biochips. The invented lipoplex nanoparticles can also be used to capture and identify cells.

DETAILED DESCRIPTION OF THE INVENTION

Definitions

As used herein, the term "nucleic acid" is a term that generally refers to a string of at least two base-sugar phosphate combinations.

As used herein, the term "nucleic acid sequence" or "oligonucleotide" also encompasses a nucleic acid and polynucleotide as defined above. The term "DNA molecule" includes nucleic acids/polynucleotides that are artificially made DNA mimic.

As used herein, the term "locked nucleic acid (LNA) or LNA nucleosides" is a class of nucleic acid analogues in which the ribose ring is "locked" by a methylene bridge connecting the 2'-O atom and the 4'-C atom in a conformation for Watson-Crick binding, which makes the pairing with a complementary nucleotide strand more rapid and more stable. The LNA has a general chemical structure described as formula (I), where the Base comprises a (i.e. A), g (i.e. G), c (i.e. C) and t (i.e. T).

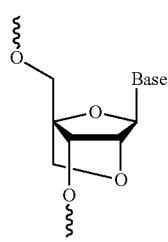

(I)

Embodiments

In one embodiment, the present invention discloses a method of detecting the presence of mutated genes, mRNAs or microRNAs in a subject. The method comprises the following steps. (1) Provide a body fluid sample containing cells, circulating tumor cells (CTCs), and/or extracellular vesicles (EVs); and use an analyzer having overhang molecular beacons to measure fluorescence signals generated by interactions between the body fluid sample and the overhang molecular beacons, so as to detect the presence of the mutated genes, mRNAs or microRNAs. The overhang molecular beacons comprises or consists of a stem having at least 9-base pairs, a loop having at least 4 bases, an overhang section of at least 5 complementary bases to the mutated genes or mRNAs at the end of the stem, a fluorescence dye and a quencher at the 3' end; and the last complementary base of the overhang section or the first complementary base of the stem in the overhang molecular beacons is corresponding to a single-point mutated base of the mutated genes, mRNAs or microRNAs.

In one example of the embodiment, the overhang molecular beacons are selected from the group consisting of SEQ ID No 2, SEQ ID No 4, SEQ ID No 5, SEQ ID No 6, SEQ ID No 7, SEQ ID No 9, SEQ ID No 11, SEQ ID No 12, SEQ ID No 13 and their combinations.

In one example of the embodiment, the SEQ ID No 4, SEQ ID No 5, SEQ ID No 6 or their combinations is applied for detecting KRAS mutations.

In one example of the embodiment, the SEQ ID No 7, SEQ ID No 9 or their combinations is applied for detecting EGFR mutations.

In one example of the embodiment, the SEQ ID No 11, SEQ ID No 12 or their combinations is applied for detecting EML4-ALK fusion.

In one example of the embodiment, the SEQ ID No 13 is applied for detecting miR-411 editions (EDs).

In one example of the embodiment, the fluorescence dye comprises FAM, Cy3 and Cy5 at the 5' end and an internal fluorescence dye comprises iFluorT, iCy3 and iCy5 close to the quencher position.

In one example of the embodiment, the overhang molecular beacons are encapsulated within lipoplex nanoparticles which comprise cationic lipoplex nanoparticles and reacts with extracelluar vesicles that are captured on the biochip surface by specific antibodies.

Typically, the lipoplex nanoparticles are made of lipid mixtures such as 1,2-di-O-octadecenyl-3-trimethylammonium propane (DOTMA), 1,2-dioleoyl-3-trimethylammonium-propane (DOTAP), 3ß-[N—(N',N'-dimethylaminoethane)-carbamoyl]cholesterol hydrochloride (DC-Cholesterol), and other ionizable lipids, 1,2-di-O-octadecenyl-3-dimethylammonium propane (DODMA), 1,2-dioleoyl-3-dimethylammonium-propane (DODAP), and other non-ionizable lipids: DODMA), L-α-phosphatidylcholine (EggPC, SoyPC), Cholesterol, 1,2-dipalmitoyl-sn-glycero-3-phosphocholine (DPPC), and other saturated fatty acid, 1,2-dioleoyl-sn-glycero-3-phosphocholine (DOPC), and other helper lipids and 1,2-distearoyl-sn-glycero-3-phosphoethanolamine-N-[methoxy(polyethylene glycol)] (DSPE-PEG), and other PEG phospholipids.

In one example of the embodiment, the lipoplex nanoparticles are tethered on biochips and universal standard vesicle (SV) nanoparticles consisting of more than 100 target oligos from mRNA and miRNA targets are added as a standard for the biochips.

In one example of the embodiment, the analyzer further comprises microfluidic channels, lipoplex nanoparticles for encapsulating the overhang molecular beacons, and a detector which comprises a total internal reflective fluorescence (TIRF) microscope, fluorescence microscope, plate reader or portable fluorescence detector.

In one example of the embodiment, wherein the mutated mRNA is corresponding to a cancer mutation comprises KRAS mutations in pancreactic cancer, EGFR mutations in non-small cell lung cancer, EML4-ALK fusion in non-small cell lung cancer.

In one example of the embodiment, wherein the body fluid sample is blood, serum, plasma, urine, sputum, or saliva from the subject.

In one example of the embodiment, the method is to detect the mutated genes, mRNAs or microRNAs in the subject with the disease or condition in a cancer which is selected from the group consisting of, but not limited to, lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colon-rectal cancers, prostatic cancer, pancreatic cancer, or cancer cachexia.

In another embodiment, the present invention provides a biochip for detecting mutated genes, mRNAs or microRNAs. The invented biochip comprises a gold coating substrate and lipoplex nanoparticles. The lipoplex nanoparticles tether on the gold coating substrate and encapsulate a plaurity of overhang molecular beacons and the overhang molecular beacons comprise or consist of a stem having at least 9-base pairs, a loop having at least 4 bases, an overhang section of at least 5 complementary bases to the mutated genes, mRNAs or microRNAs at the end of the stem, a fluorescence dye and a quencher at the 3' end; and wherein the last complementary base of the overhang section or the first complementary base of the stem in the overhang molecular beacons is corresponding to a single-point mutated base of the mutated gene, mRNAs, or microRNAs.

In one example of the another embodiment, the overhang molecular beacons are selected from the group consisting of SEQ ID No 2, SEQ ID No 4, SEQ ID No 5, SEQ ID No 6, SEQ ID No 7, SEQ ID No 9, SEQ ID No 11, SEQ ID No 12 SEQ ID No 13 and their combinations.

In one example of the another embodiment, the SEQ ID No 4, SEQ ID No 5, SEQ ID No 6 or their combinations is applied for detecting KRAS mutations.

In one example of the another embodiment, the SEQ ID No 7, SEQ ID No 9 or their combinations is applied for detecting EGFR mutations.

In one example of the another embodiment, the SEQ ID No 11, SEQ ID No 12 or their combinations is applied for detecting EML4-ALK fusion.

In one example of the another embodiment, the SEQ ID No 13 is applied for detecting miR-411 editions (EDs).

In one example of the another embodiment, the fluorescence dye comprises FAM, Cy3 and Cy5 at the 5' end and an internal fluorescence dye comprises iFluorT, iCy3 and iCy5 close to the quencher position.

In one example of the another embodiment, the quencher at the 3' end comprises BHQ-1 and BHQ-2.

The following examples are to disclose and interpret the present invention in details.

Example 1—CLN-TIRF Technology and MB Design

Figure 1B:
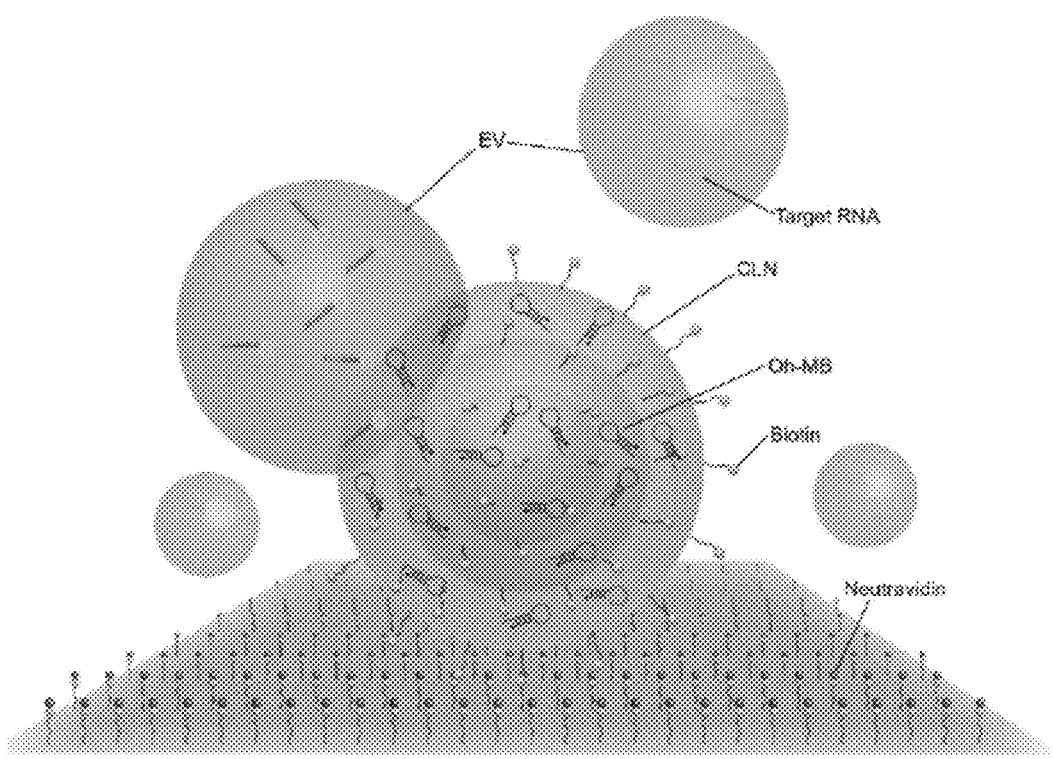

FIG. 1A shows an overall illustration of CLN-TIRF technology. As zoomed in FIG. 1B, specific MBs for RNA targets are designed and encapsulated in CLNs which are then linked onto a chip through biotin-avidin interaction to capture negatively charged EVs from any liquid sample such as cell culture medium or human serum/plasma by electrostatic interactions to form larger nanoscale complexes. The subsequent CLN-EV fusion leads to mixing of MBs in the CLN with miRNAs/mRNAs in the EVs near the chip surface. CLNs and EVs are around 100 nm, which makes them diffraction limited, and relatively low signal given off by MBs near surface requires a specific microscope system. Fluorescence signals of MBs after their binding to target RNAs are observed by the total internal reflection fluorescence (TIRF) microscopy, which has high sensitivity for detecting a single biomolecule less than 300 nm distance from the interface. CLN realizes the encapsulated MBs binding with RNA targets in EVs without breaking the lipid bilayer of EVs, comparing to qRT-PCR which needs to extract miRNAs/mRNAs by breaking EVs or cells prior to analysis.

Figure 1C:
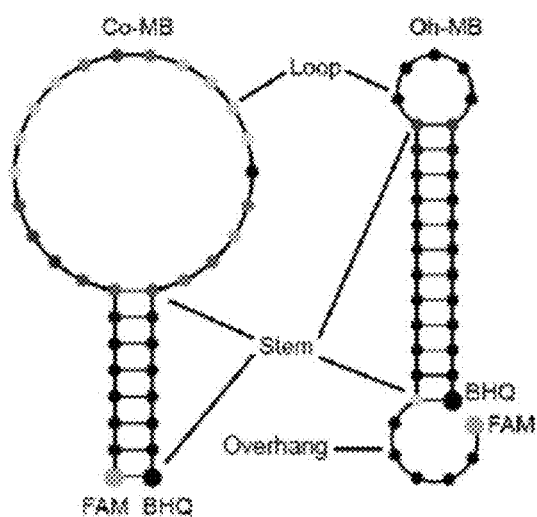
Figure 1D:
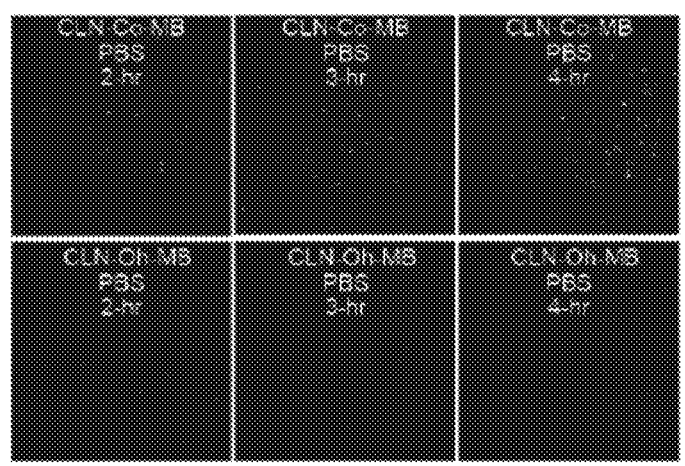
Figure 1E:
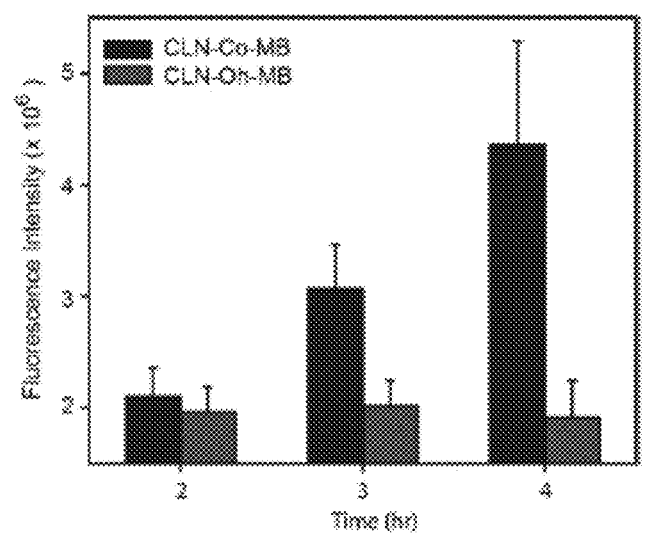

For clinical use, CLN-MB biochips need to be mass produced with long-term storage stability in both liquid and dry form. This requires stable MBs in CLNs. As shown in FIG. 1C (left), the Co-MB is an oligonucleotide probe consisting of 7-base pair stem and 22-nucleotide loop with a free energy ΔG of −7.32 kcal/mol at 37° C., for miR-21 RNA target. A newly designed Oh-MB, as shown in FIG. 1C (right), has a 12-base pair stem and a 6-nucleotide loop. In comparison to Co-MB, an overhang section of 6 complementary bases to target RNA is added at the end of the stem of Oh-MB. The free energy ΔG of the newly designed Oh-MB is −10.31 kcal/mol at 37° C. for miR-21 RNA target. There are three advantages of Oh-MB over Co-MB in CLNs: first, the 12-base pair stem of Oh-MB is much more stable in CLNs due to its lower free energy in comparison to the 7-based pair stem of Co-MB. Secondly, the 6-nucleotide loop of Oh-MB is less likely to be denatured because of its more compact structure comparing to the 22-nucleotide loop of Co-MB. Finally, the 6-nucleotide overhang section could initiate a quick hybridization of the 12-base stem strand with the target RNA strand because of its high reaction rate constant ($10^6$~$10^7$ M−1 s$^{-1}$). Without hybridization with the target RNA, Co-MB is more likely to be denatured than Oh-MB in CLNs when incubated in PBS at 37° C. for 2, 3 and 4 h (FIG. 1D). FIG. 1E shows the linear comparison of the stability of CLN-Co-MB and CLN-Oh-MB for over 4 h in PBS at 37° C. The fluorescence signal at 4 h was doubled comparing to that at 2 h for CLN-Co-MB. By contrast, CLN-Oh-MB could remain stable in the liquid form in 4 h. Comparing with Co-MB, the higher stability of Oh-MB in CLNs led to a lower background fluorescence caused by denaturation of secondary hairpin structure. This is advantageous for a higher sensitivity gain and for an improved signal to background ratio.

Example 2—Comparison of CLN-Co-MB and CLN-Oh-MB Based on Standard Vesicles (SVs)

Figure 2A:
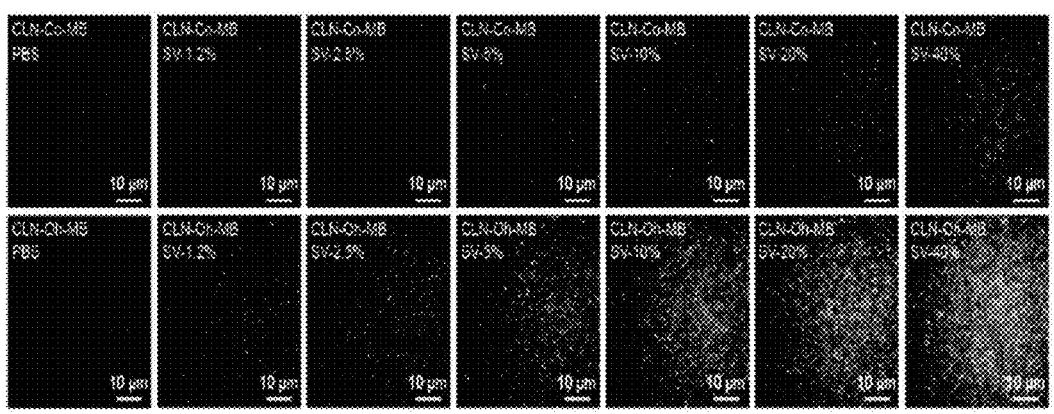
FIGS. 2A-2F show Performance of CLN-Co-MB and CLN-Oh-MB based on standard vesicles (SVs)
Figure 2B:
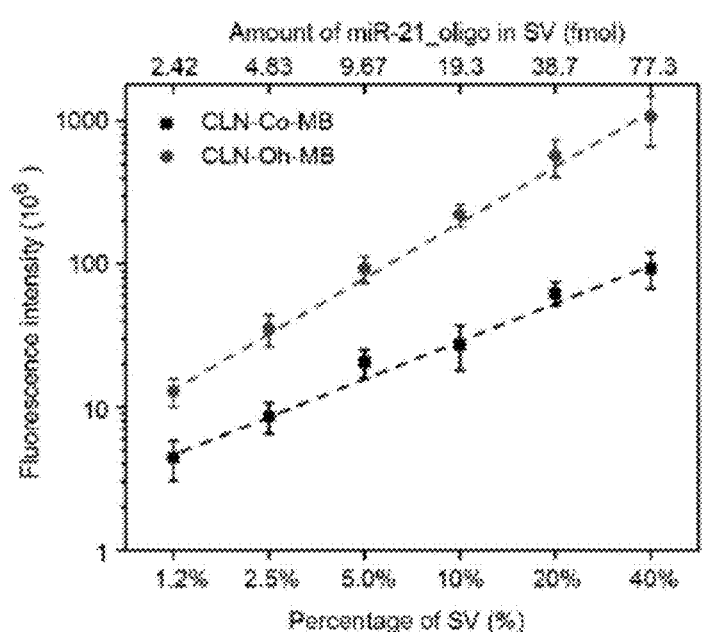
Figure 2C:
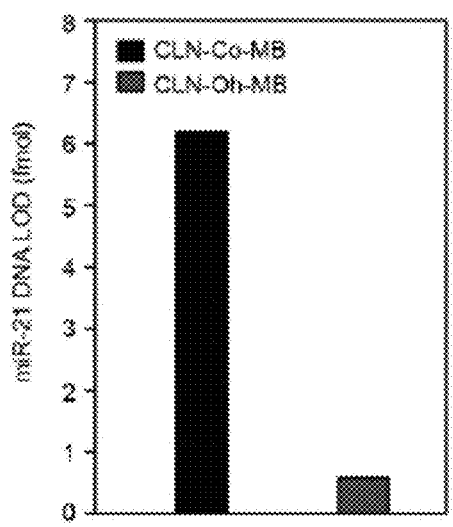
Figure 2D:
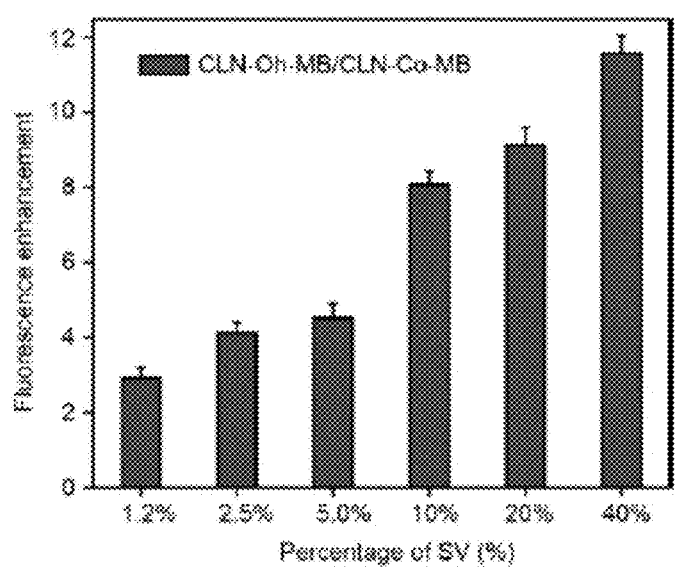

To develop a standard for chip-to-chip calibration and normalization, standard vesicles (SVs) made of anionic lipoplex nanoparticles containing miR-21_oligo DNAs were prepared to mimic the real EVs with a similar particle diameter (50~150 nm) and a slightly negative surface charge (−8.7 mV) (Table 1). Since the target RNA in EVs has a small copy number along with other RNAs, we prepared SVs containing 1% of single strand miR-21_oligo DNA mixed with 99% of low-cost miR-54_oligo DNA (scramble DNA). Initial testing of the hybridization efficacy of CLN-MB biochips with target RNAs was carried out using SVs. The SV concentration analyzed by Nanosight™ was $3 \times 10^{10}$/mL and the calculated average copy number of encapsulated miR-21_oligo was around 50-200 strands per SV. Results of CLN-Co-MB and CLN-Oh-MB comparison based on SVs are shown in FIG. 2. Representative TIRF fluorescence images and calibration curves revealed an increase of the fluorescence signal of miR-21_oligo expression in SVs in proportion to the SV concentration (1.2%~40% dilution equal to 30~1200×10$^7$/mL) for both CLN-Co-MB and CLN-Oh-MB (FIGS. 2A, B). The high specificity of both Co-MB and Oh-MB was demonstrated by the negligible fluorescence signal for SVs encapsulating 100% scramble DNAs, which is similar to that in PBS (data not shown). The linear increase of fluorescence intensity in proportion to the SV concentration for both CLN-Co-MB and CLN-Oh-MB confirmed the robustness and precision of the CLN-TIRF technology. The linearly extrapolated limit of detection (LOD) for miR-21_oligo was calculated to be about 3 fmol and 0.3 fmol for CLN-Co-MB and CLN-Oh-MB, respectively, based on the detection limit and the encapsulation efficiency of SV (FIG. 2C, Table 2). CLN-Oh-MB exhibited fluorescence enhancement over CLN-Co-MB at each SV concentration, reaching 3- and 12-fold at 1.2% and 40% of SVs, respectively (FIG. 2D). These results demonstrated the superior target recognition and hybridization efficiency of CLN-Oh-MB over CLN-Co-MB, which was probably attributed to the higher reaction rate of Oh-MB when hybridizing with target RNA.

TABLE 2

| Formulation | Particle concentration (/mL) | Average size (nm) | Polydispersity index | Zeta potential (mV) | EE (%) |
|---|---|---|---|---|---|
| CLN-F-ODN | 5.3 × 10$^{10}$ | 102.5 ± 8.2 | 0.146 ± 0.014 | 26.2 ± 1.2 | 80.51 ± 0.36 |
| SV-F-ODN | 3.0 × 10$^9$ | 83.2 ± 11.6 | 0.153 ± 0.017 | −8.7 ± 0.5 | 58.05 ± 0.32 |

All Values Indicate Mean±S.D. for n=3 Independent Experiments

Figure 2E:
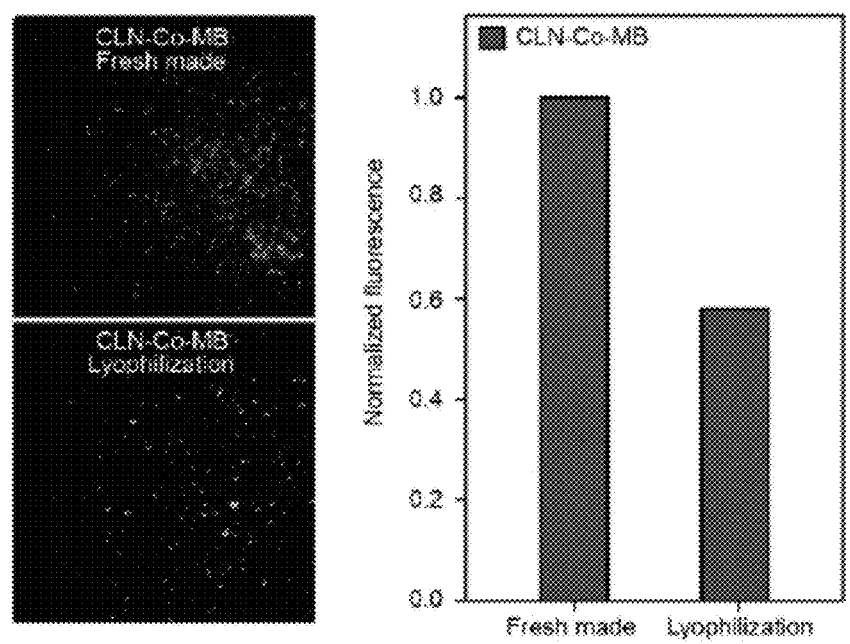
Figure 2F:
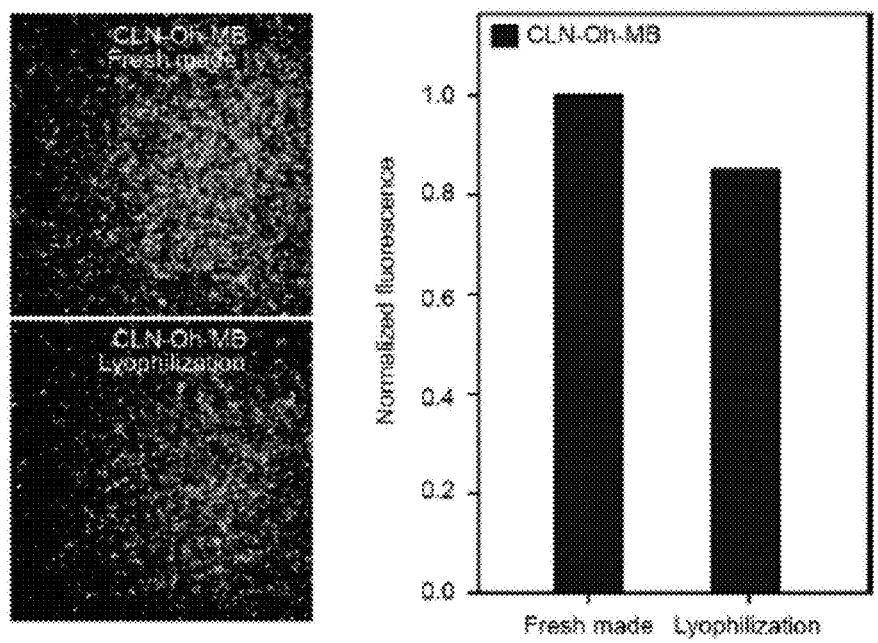

For clinical applications, users prefer to use the pre-synthesized CLN-MB to simplify the assay. Lyophilization is a widely used method to prepare the dry form of lipoplex nanoparticles. FIGS. 2E and 2F show the comparison of fluorescence signals between the fresh-made and lyophilized CLN-Co-MB or CLN-Oh-MB incubating with 40% of SVs at 37° C. for 2 h. Lyophilized CLN-Co-MB only maintained ~60% of the signal in comparison to fresh-made CLN-Co-MB, while the signal from lyophilized CLN-Oh-MB was recovered by 83%. This result indicates lyophilization feasibility of CLN-Oh-MB for large scale clinic use.

Figure 2G:
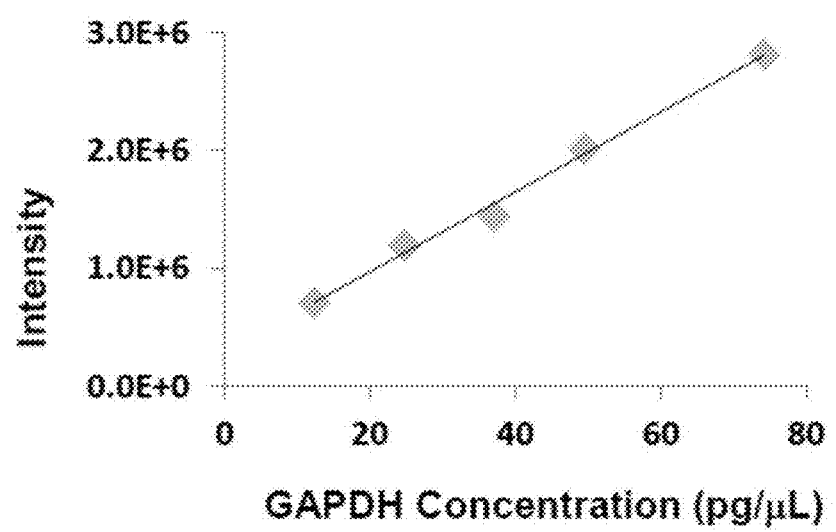
FIG. 2G is Calibration and analytical quantification curve for CLN fluorescence using SVs and qRT-PCR.

We have determined the concentration of target RNAs through calibration and analytical quantification curve for total fluorescence intensity of GAPDH mRNA in EVs. The concentration of GAPDH mRNA was also determined by using standard vesicles (SVs) with GAPDH fragment oligo. The SVs with GAPDH oligo target were prepared and sequentially diluted to produce SV solutions with different contents of GAPDH fragment target. The calibration curve was determined by CLN-TIRF assay. As shown in FIG. 2G, the total fluorescence intensity (TFI) measured from 100 TIRF images using the CLNs on our CLN biochip by TIRF microscopy shows a linear relationship vs. the SV content. The concentration of GAPDH oligo target can also be measured and confirmed by q-PCR. Both CLN biochip assay and q-PCR showed a good agreement.

Example 3—Comparison of CLN-Co-MB and CLN-Oh-MB in Cancer Cells

Figure 3A:
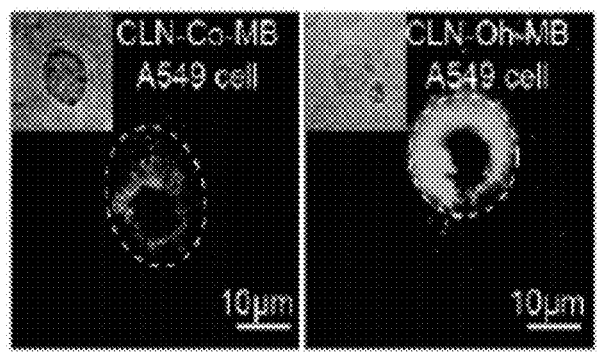
FIGS. 3A-3J are Comparison of CLN-Co-MB and CLN-Oh-MB for miR-21 expression in cells and cell secreted EVs.
Figure 3B:
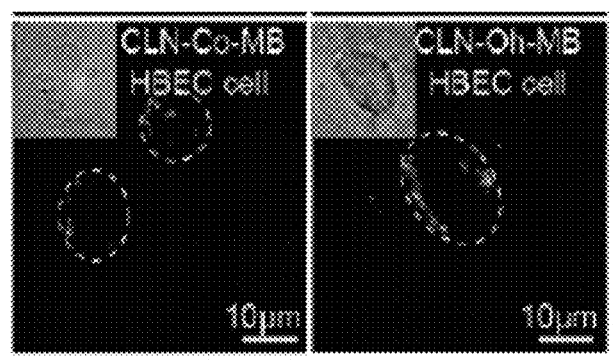
Figure 3C:
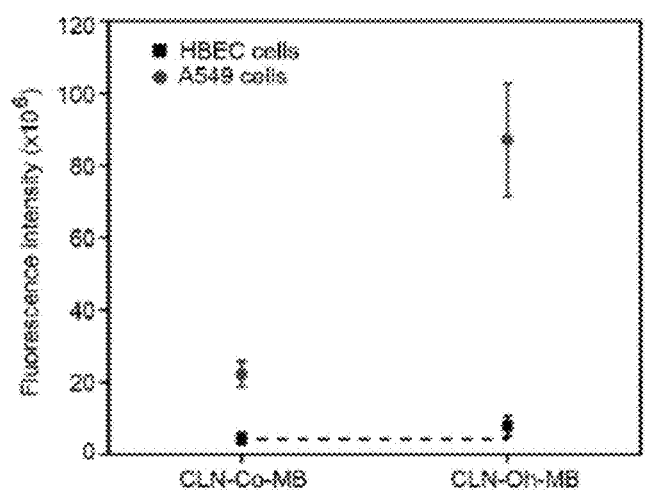
Figure 3D:
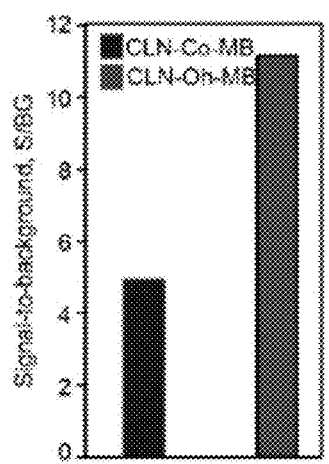
Figure 3E:
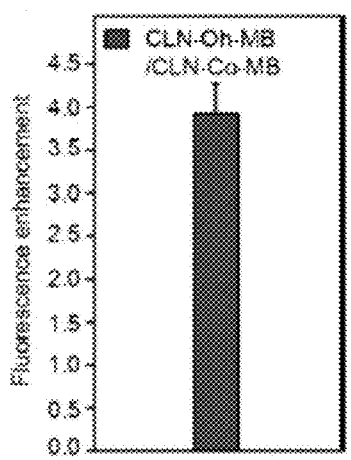

We then compared CLN-Co-MB and CLN-Oh-MB in living cells. The miR-21, which is often overexpressed in tumor cells, was chosen as a target model. A549, which is a lung cancer cell line with overexpressed miR-21, was chosen as the test cell. HBEC, which is normal human bronchial epithelial cell line, was chosen as the negative control cell. After loading A549 or HBEC cells onto the CLN biochip, CLNs were internalized by the cells, and the subsequent release of MBs could detect the intracellular target RNAs. FIG. 3 shows the comparison of live cell imaging in A549 and HBEC cell lines with CLN-Co-MB and CLN-Oh-MB. Stronger fluorescence signals from the A549 cells were observed, comparing to the control HBEC cells (inside upper left figure was phase contrast image of each single cell). The superior recognition efficacy of CLN-Oh-MB against CLN-Co-MB can be clearly seen in FIGS. 3A and 3B. Further quantitative analysis of image data showed that the fluorescence intensity of A549 cells with CLN-Oh-MB was much higher than that with CLN-Co-MB, whereas their backgrounds (HBEC cells) differed slightly (FIG. 3C). The large increase in signal with only a modest increase in background provided an excellent signal-to-background (SB) ratio for CLN-Oh-MB as shown in FIG. 3D. This led to a 4-fold fluorescence enhancement over CLN-Co-MB by CLN-Oh-MB (FIG. 3E).

Example 4—Comparison of CLN-Co-MB and CLN-Oh-MB in Cancer EVs

Figure 3F:
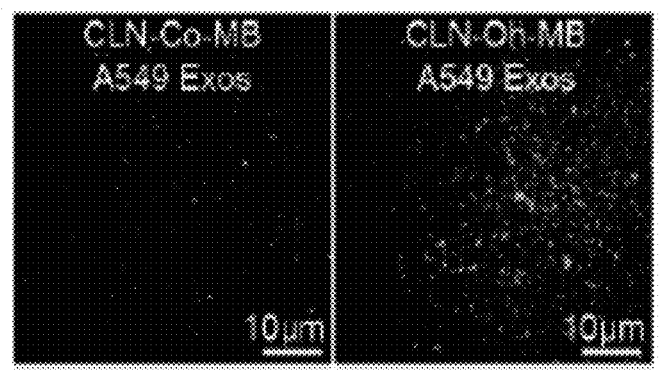
Figure 3G:
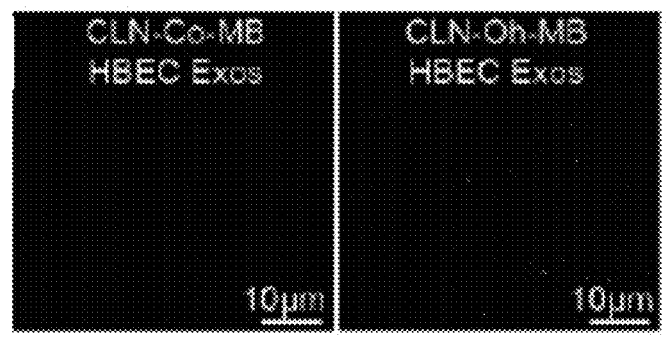
Figure 3H:
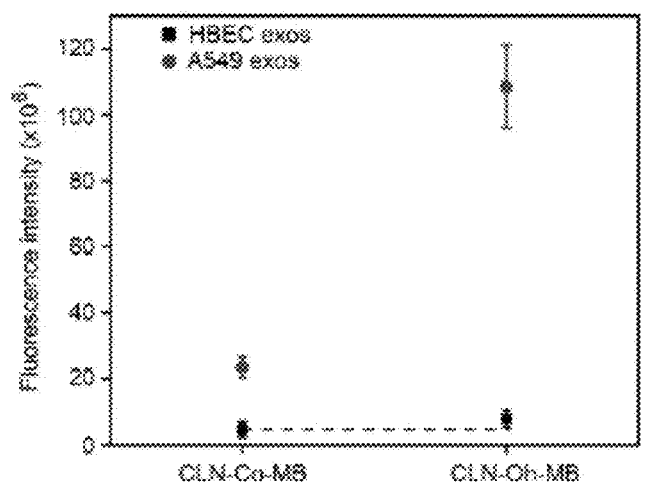
Figure 3I:
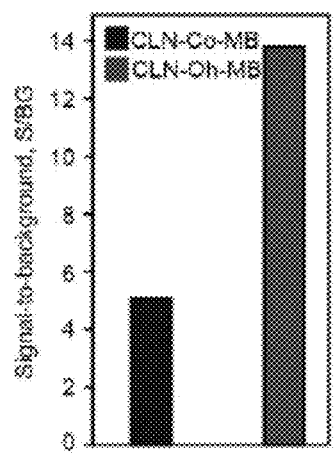
Figure 3J:
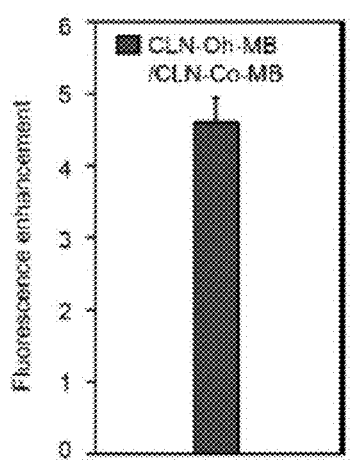

EVs collected from A549 or HBEC cell culture medium were directly applied to the CLN biochip containing miR-21-specific CLN-Co-MBs or CLN-Oh-MBs. The EV concentration was around 10$^7$/mL (2×10$^5$ EVs in 20 μL) in cell culture medium. As shown in FIGS. 3F and 3G, stronger fluorescence signals from A549 cells-derived EVs were observed in comparison to negligible fluorescence signals from HBEC cells-derived EVs. Quantitative results showed that the fluorescence signal of miR-21 expression in A549 EVs detected by CLN-Oh-MB was much higher than that by CLN-Co-MB (FIG. 3H). FIG. 3I shows a 5- and 14-fold higher fluorescence intensity of A549 EVs compared to HBEC EVs by CLN-Co-MB and CLN-Oh-MB, respectively. Statistical analysis of the imaging data from A549 cell culture medium with CLN-Oh-MB showed a 4.5-fold increase in fluorescence intensity over that with CLN-Co-MB (FIG. 3J). These results demonstrated that the new CLN-Oh-MB can provide a significant improvement in sensitivity of the assay.

Example 5—Comparison of CLN-Co-MB and CLN-Oh-MB in Single-Point Mutation

Figure 4A:
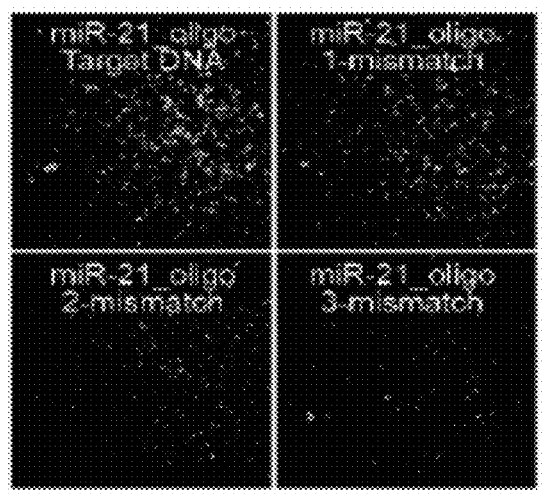
FIGS. 4A-4J are Comparison of CLN-Co-MB and CLN-Oh-MB in single-base mutation.
Figure 4B:
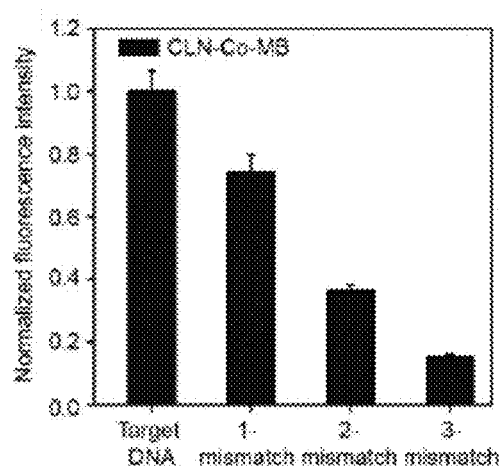
Figure 4C:
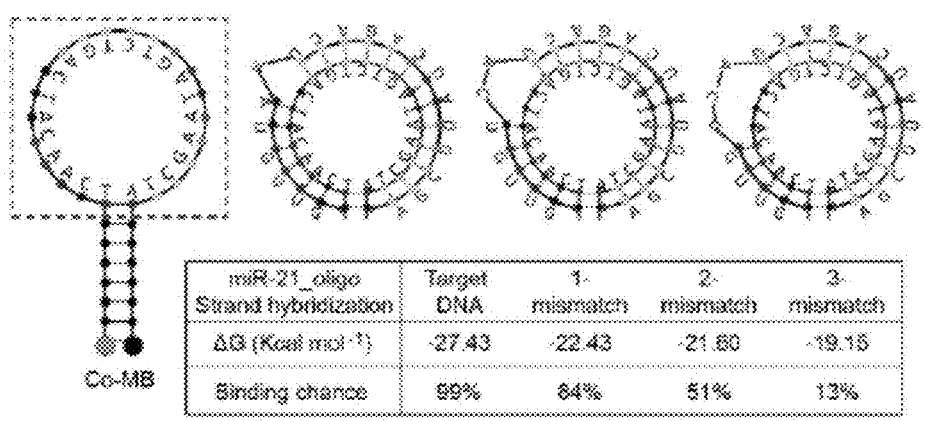
Figure 4D:
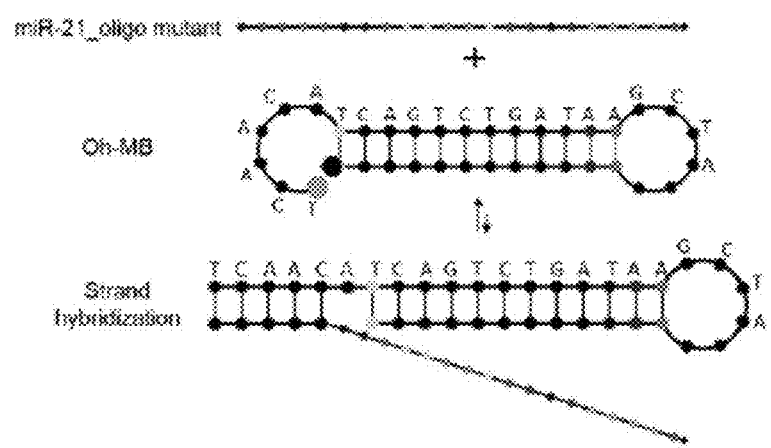
Figure 4E:
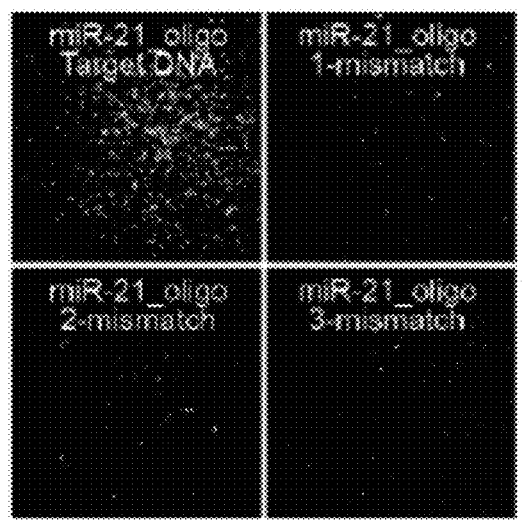
Figure 4F:
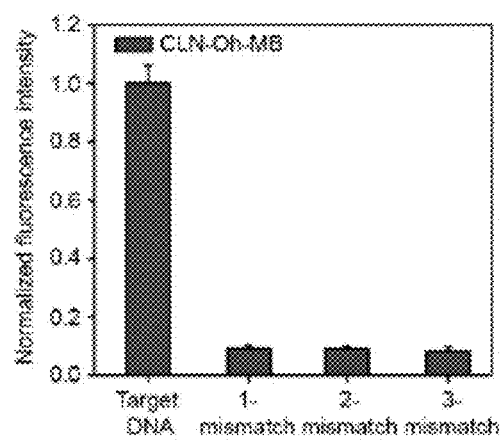

The CLN-Co-MB has been studied for single-point mutation detection in surveillance of cancer therapy, but could not provide the needed specificity. Here, we first encapsulated miR-21_oligo wide-type, single mutant (1-base mismatch), bi-mutant (2-base mismatch) and tri-mutant (3-base mismatch) in SVs as a model system to compare CLN-Oh-MB and CLN-Co-MB. FIG. 4A shows the representative TIRF images of SVs containing miR-21_oligo mutants detected by CLN-Co-MB. Statistical analysis of image data showed the strongest fluorescence signal from miR-21_oligo wide-type as expected. However, miR-21_oligo single mutant, bi-mutant and tri-mutant also showed 75%, 37% and 15% of fluorescence signal, respectively (FIG. 4B). The standard free energy (ΔG) of a reaction can be calculated by subtracting the standard free energies of formation of the reactants from that of the products: $\Delta G° = \Sigma_{i=1}^{n} \Delta G°$(Product i) $- \Sigma_{i=1}^{m} \Delta G°$(Reactant i). Using the standard free energies of DNA/RNA strands and complexes, we can calculate the standard free energies of various reactions based on Watson-Crick base pairing, which in turn allows us to calculate the reaction equilibrium constants and hybridization probability. FIG. 4C illustrates the mutant hybridization and theoretical calculation of free energy and binding chance for Co-MB. Experimental results matched well with the calculated binding chance (Table in FIG. 4C), revealing that CLN-Co-MB failed to identify the mutants with less than 3-base mismatch. Based on this knowledge, CLN-Oh-MB was designed for single-point mutation detection. For the miR-21_oligo mutants, the locations of mutated bases are shown in FIG. 4D, marked in red color. The miR-21_oligo mutant strand would first bind to the Oh-MB via TCAACA, forming an intermediate complex (FIG. 4D, bottom). Importantly, branch migration is not a directed process, but rather a random walk. From the state of intermediate complex, there is an equal probability of taking step forward to hybridize with the sixth base (A) and of taking a step backward to dissociate the fifth base (C). When branch migration reaches the mutant base, the dissociation rate ($k_r$) of the intermediate complex is larger than the hybridization rate ($k_f$), especially when the number of newly formed base pairs is fewer than that of stem base pairs. Comparing to the image of miR-21_oligo wide-type, the bright spots were much fewer in images of miR-21_oligo single mutant, bi-mutant and tri-mutant expression in SVs by using CLN-Oh-MB (FIG. 4E). FIG. 4F shows the normalized signal intensity comparison, the fluorescence signal of single mutant only reached 3% of that of miR-21_oligo wide-type, indicating that CLN-Oh-MB could quickly and precisely distinguish the wild-type nucleotide sequence from the single mismatch mutant because the designed structure would stop the hybridization reaction between the MB sequence and the mutant sequence.

Figure 4G:
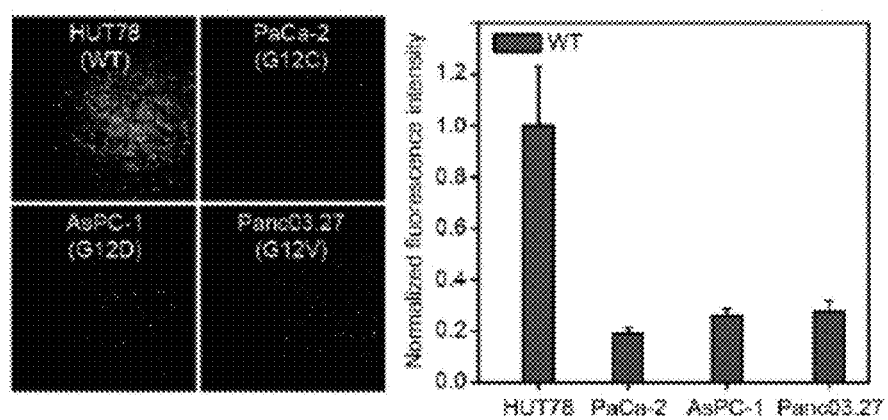
Figure 4H:
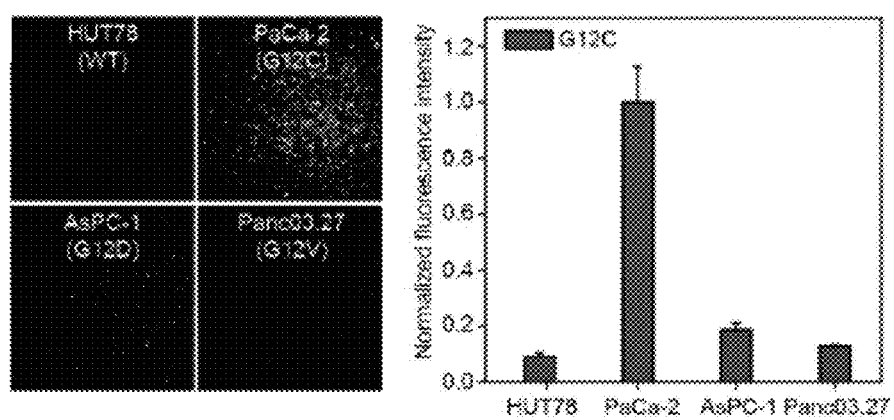
Figure 4I:
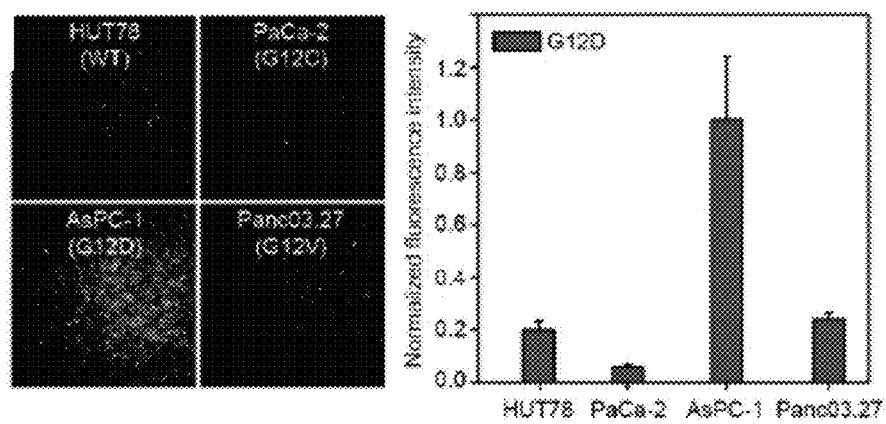
Figure 4J:
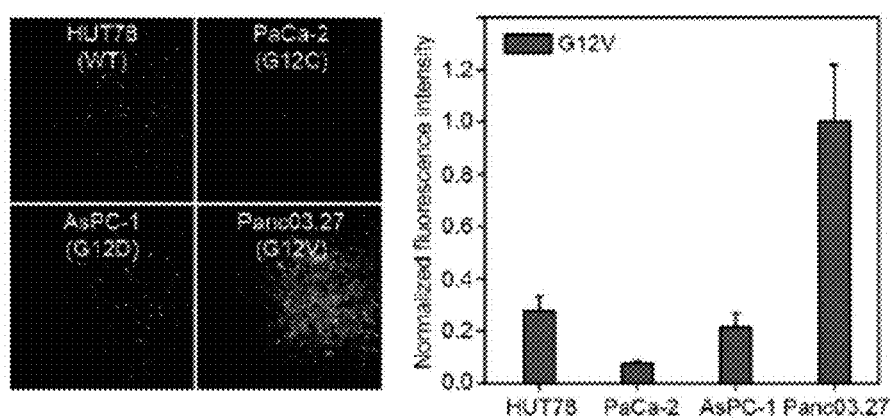

Based on these results, we further verified the efficacy of CLN-Oh-MB for three important KRAS mutants (G12C, G12D, G12V), which count for >65% of pancreatic cancer patients. The locations of mutated base were marked in gray color as shown in Table 3. The Oh-MB$^{WT}$, Oh-mBG-$^{G12C}$, Oh-MB$^{G12D}$ and Oh-MB$^{G12V}$ were designed to complement with KRAS$^{WT}$, KRAS$^{G12C}$, KRAS$^{G12D}$ and KRAS$^{G12V}$, respectively (Table 3). Four pancreatic cancer cell lines, HUT78, PaCa-2, AsPC-1 and PANC03.27 known as a wild-type (WT), G12C, G12D and G12V mutation respectively, were used as the model systems. EVs collected from cell culture medium were directly applied to the CLN-Oh-MB tethered biochips. Compare to KRAS$^{WT}$, the fluorescence signals of KRAS$^{G12C}$, KRAS$^{G12D}$ and KRAS$^{G12V}$ with CLN-Oh-MB$^{WT}$ were reduced to 2%, 7% and 15%, respectively (FIG. 4G). By using CLN-Oh-MB$^{G12C}$, the fluorescence signals of KRAS$^{WT}$, KRAS$^{G12D}$ and KRAS$^{G12V}$ only reached 12%, 11% and 9% of that of KRAS$^{G12C}$ as shown in FIG. 4H. Similar results for KRAS$^{G12D}$ and KRAS$^{G12V}$ are shown in FIGS. 4I and 4J respectively. These results indicate that our CLN-Oh-MB design is unique that it is capable of direct identification of single-point mutations in living cells and their secreted EVs.

TABLE 3

| Name | DNA sequence, listed 5' to 3' |
| --- | --- |
| miR-54_oligo | AGGATATGAGACGACGAGAACA |
| miR-21_oligo Target | TAGCTTATCAGACTGATGTTGA |

TABLE 3-continued

| Name | DNA sequence, listed 5' to 3' |
| --- | --- |
| miR-21_oligo 1-mismatch | TAGCTTATCAGACTAATGTTGA |
| miR-21_oligo 2-mismatch | TAGCTTATCAGACTACTGTTGA |
| miR-21_oligo 3-mismatch | TAGCTTATCAGACTACCGTTGA |
| Co-MB-miR21 | /6FAM/CGCGATCTCA[+A]CA[+T]CA[+G]TC[+T]GA[+T]-AA[+G]CTAGATCGCG/BHQ1/ |
| Oh-MB-miR21 | /6FAM/(+T]CA[+A]CA[+T]CA[+G]TC[+T]GA[+T]AA[+G]C-T[+A]GATTATCAGACTGA/BHQ1/ |
| Oh-MB-KRAS$^{WT}$ | /6FAM/CC[+T]AC[+G]CC[+A]CC[+A]GC[+T]CC[+A]AC[+T]AATGGAGCTGGTGG/BHQ1/ |
| Oh-MB KRAS$^{G12C}$ | /6FAM/CG[+C]CA[+C]AA[+G]CT[+C]CA[+A]CT[+A]CC[+A]CTTAGTTGGAGCTT/BHQ1/ |
| Oh-M8-KRAS$^{G12D}$ | /6FAM/AC[+G]CC[+A]TC[+A]GC[+T]CC[+A]AC[+T]AC[+C]ACGAGTTGGAGCTGA/BHQ1/ |
| Oh-MB-KRAS$^{G12V}$ | /6FAM/AC[+G]CC[+A]AC[+A]GC[+T]CC[+A]AC[+T]AC[+C]AGAGTTGGAGCTGT/BHQ1/ |

Figure 5A:
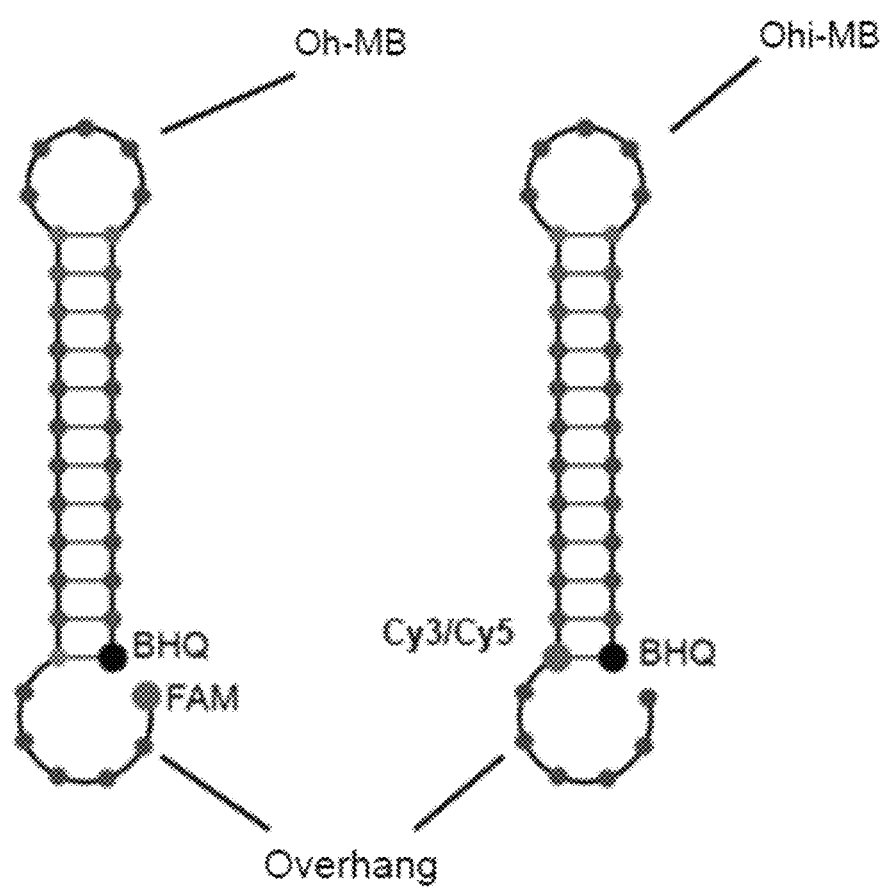
FIG. 5A is Structure of Oh-MBs. External dye containing Oh-MB (left) and internal dye containing Ohi-MB (right)

Example 6—Design of CLN-Ohi-MB for Improvement of Single-Point Mutation Detection The CLN-Oh-MB developed for single-point mutation detection in early cancer diagnosis has a high background noise due to an external dye and quencher structure. To reduce the background noise from the external dye in the end of overhang section of Oh-MBs, internal fluorescence dye close to the quencher position was designed into the MB construct. Here, we show Ohi-MBs made of Cy3 or Cy5 dye to serve as internal fluorophores. A typical Ohi-MB includes 3'-Black Hole Quencher 2 (3BHQ-2) to serve as a quencher of fluorogenic dual-labeled probes as shown in FIG. 5A. To achieve high stability and nuclease resistance, locked nucleic acid (LNA) nucleotides were also introduced into MBs. The designs of Ohi-MBs used in this example for targeting EGFR mRNA and EML4-ALK fusion are shown in Table 1. The squared bases indicate the LNA nucleotides.

Figure 5B:
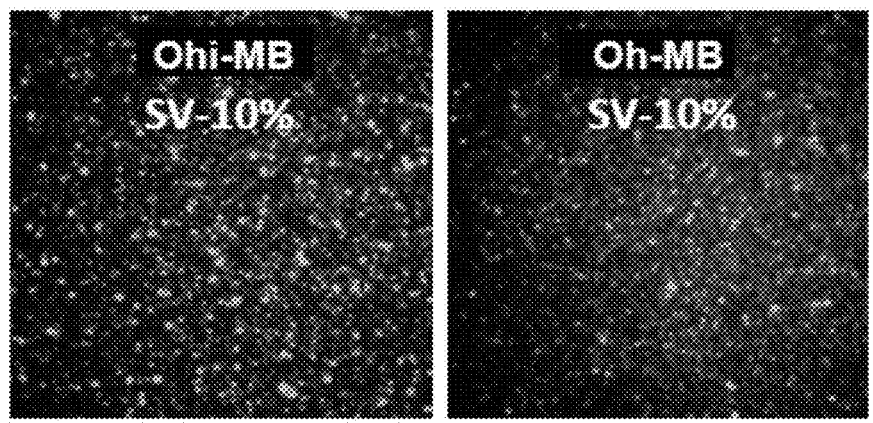
FIG. 5B and FIG. 5C are Typical TIRF images of EGFR T790M mutation and total fluorescence intensity scatter plots in concentrations of SVs (0, 5%, 10%, 20% and 40%) detected by using CLN-Ohi-MB and CLN-Oh-MB, respectively.
Figure 5C:
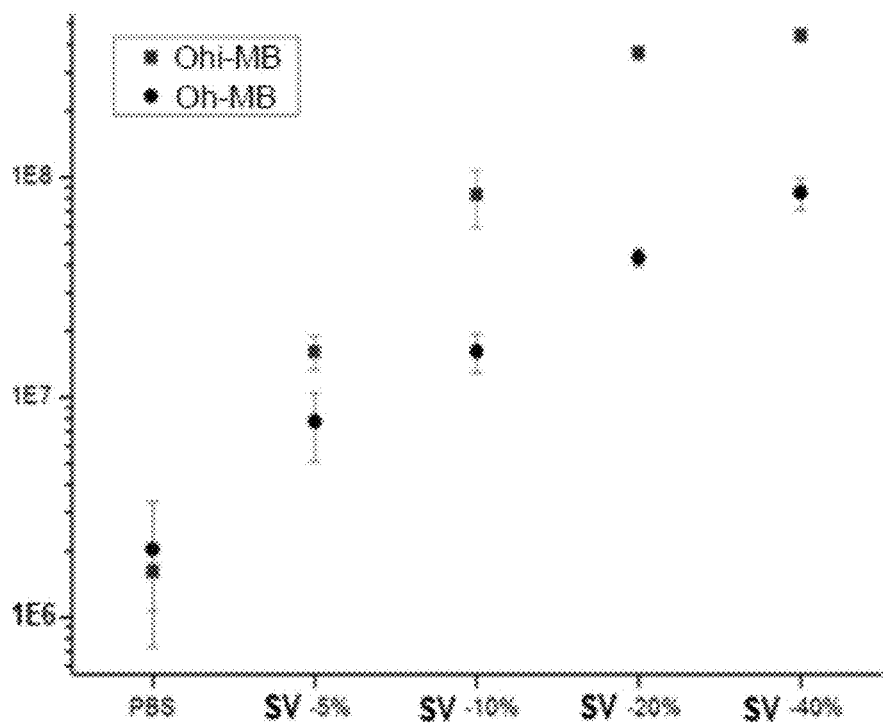

The superior recognition efficacy of Ohi-MB against the Oh-MB can be clearly seen in fluorescence images in FIG. 5B. Further quantitative analysis of image data showed that the fluorescence intensity of SVs with CLN-Ohi-MB was much higher than that with CLN-Oh-MB. The large increase in signal with only a modest increase in background noise provided an excellent signal-to-noise (S/N) ratio for CLN-Ohi-MB as shown in FIG. 5C. This led to a 3-fold fluorescence enhancement over CLN-Oh-MB by CLN-Ohi-MB.

Figure 6A:
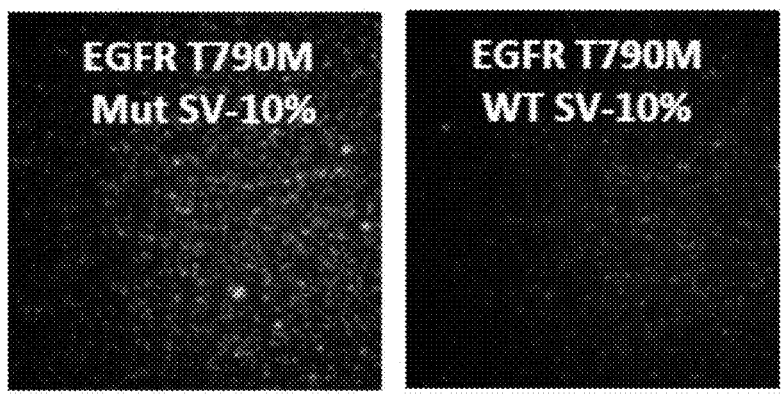
FIG. 6A and FIG. 6B are Total fluorescence intensity scatter plots and typical TIRF images of EGFR T790M mutation detected by CLN-Ohi-MB in SVs (5%, 10%, 15% and 20%) detected by using CLN-Ohi-MB EGFR T790M (WT) and CLN-Oh-MB EGFR T790M (Mut), respectively.
Figure 6B:
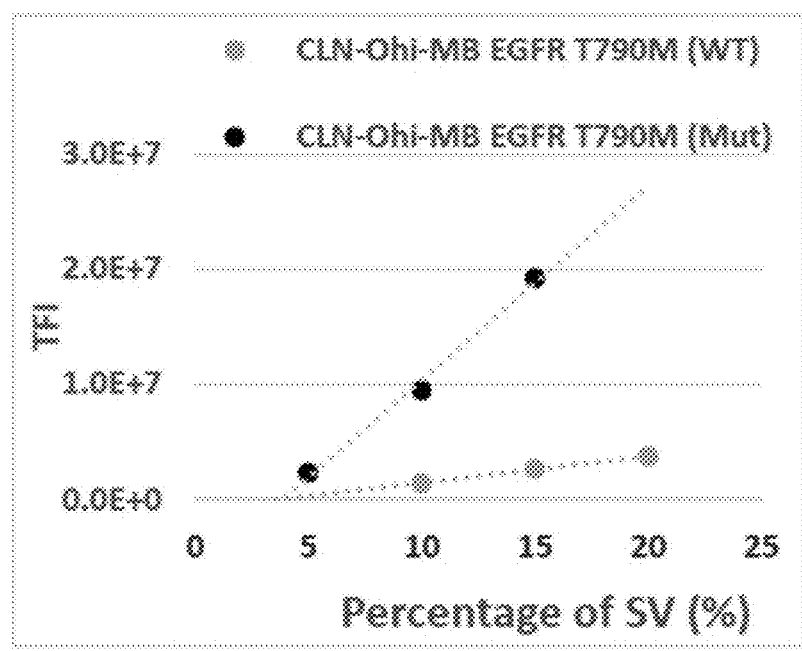
Figure 6C:
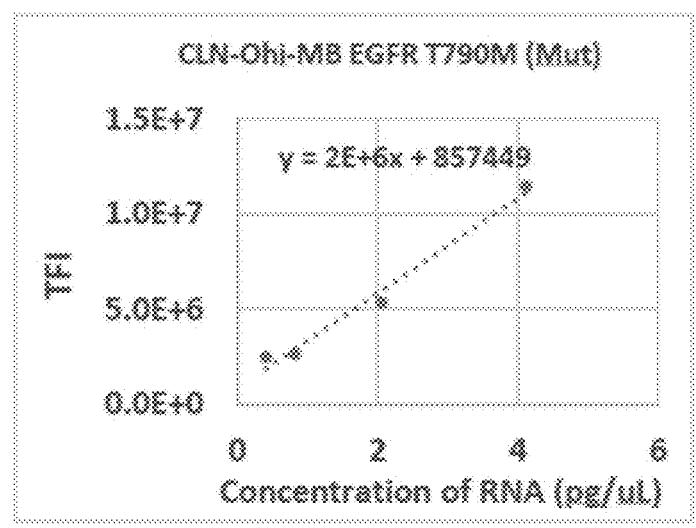
FIG. 6C, FIG. 6D and FIG. 6E are Calibration and analytical quantification curve for CLN fluorescence using SV and concentration of target RNA bar charts of EGFR L858R and T790M mutations detected by CLN-Ohi-MB in EVs collected from lung cancer cell lines (H1975 with EGFR L858R and T790M mutations, and A549 without mutations, and typical TIRF images of EGFR L858R and T790M mutations detected by CLN-Ohi-MB in EVs), respectively.
Figure 6D:
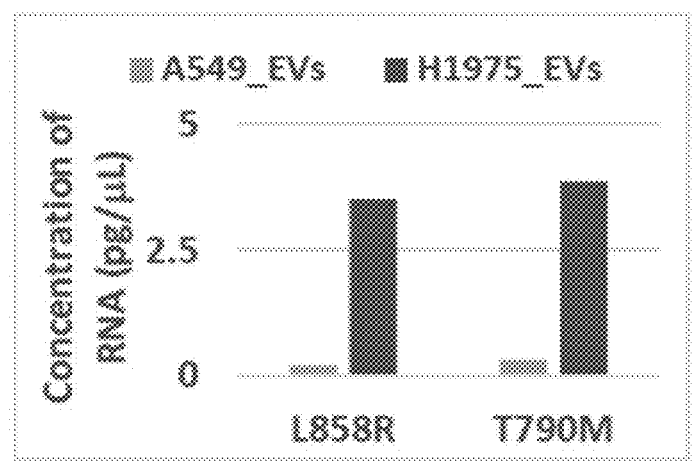
Figure 6E:
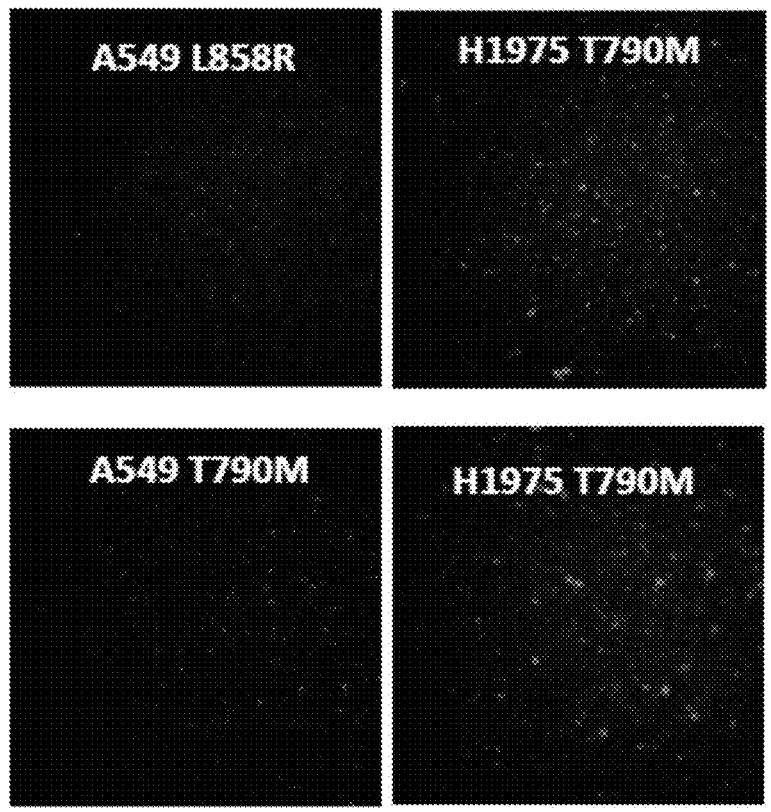
Figure 6F:
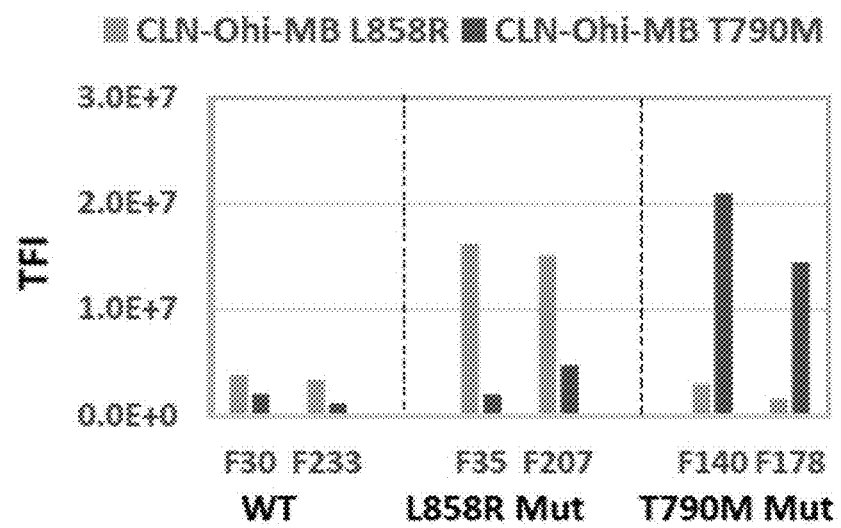
FIG. 6F and FIG. 6G are TIRF images and total fluorescence intensity bar charts of EGFR L858R and T790M mutations detected by CLN-Ohi-MB in EVs collected from small cell lung cancer patients with known EGFR mutations, respectively.
Figure 6G:
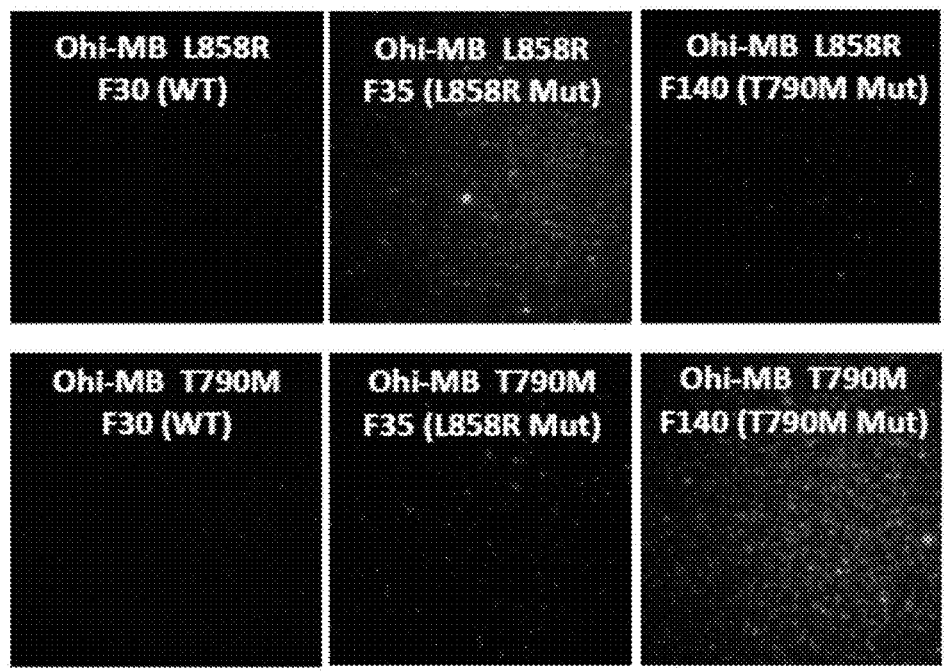

Example 7—Design of CLN-Ohi-MB for EGFR Single-Point Mutation and EML4-ALK Fusion Detection In order to improve EGFR single-point mutation detection, the internal Oh-MB (Ohi-MB) has been developed for EFGR L858R and EGFR T790M mutation. Representative TIRF fluorescence images and calibration curves revealed an increase of the fluorescence signal of T790M oligos in SVs in proportion to the SV concentration (5%, 10%, 15% and 20%) detected by using CLN-Ohi-MB EGFR T790M (WT) and CLN-Oh-MB EGFR T790M (Mut) as shown in FIGS. 6A and 6B, respectively. For further investigation of CLN-Ohi-MB, we established the calibration and analytical quantification curve for CLN fluorescence using SVs and compared the concentration of target RNA in bar charts for EGFR L858R and T790M mutations detected by CLN-Ohi-MB from EVs collected from lung cancer cell lines (H1975 with EGFR L858R and T790M mutations, and A549 without mutations) as shown in FIGS. 6C and 6D respectively. The limit of detection (LOD) was calculated to be less than a concentration of 1 pg/L for CLN-Ohi-MB. Typical TIRF images of EGFR L858R and T790M mutations detected by CLN-Ohi-MB in EVs are shown in FIG. 6E. EGFR L858R and T790M mutations were also detected by CLN-Ohi-MB in blood EVs collected from small cell lung cancer patients as shown in TIRF images and total fluorescence intensity bar charts (FIGS. 6F and 6G). Even though the patient sample number was small, the high specificity of both EGFR L858R and T790M mutation detection was demonstrated by using the CLN-Ohi-MB. These results demonstrated the superior target recognition and hybridization efficiency of CLN-Ohi-MB with a high S/N ratio.

For further investigation of the CLN-Ohi-MB performance, EML4-ALK fusion detection was conducted with MB designs shown in Table 1 in EVs collected from lung cancer cell lines (H3122 with EML4-ALK fusion variant 3a, H2228 with variant v1 and Calu-1 without EML4-ALK fusion). The results demonstrated the superior fusion variant recognition.

Figure 7A:
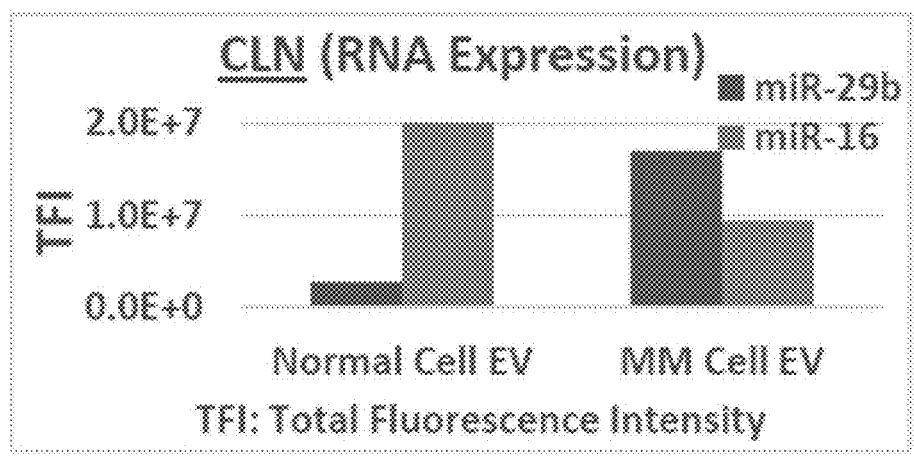
FIG. 7A is Total fluorescence intensity of two microRNAs (miR-16 and niR-29b) in EVs secreted from a healthy donor cell and multiple myeloma (MM) patient blood cell detected by CLN biochips.
Figure 7B:
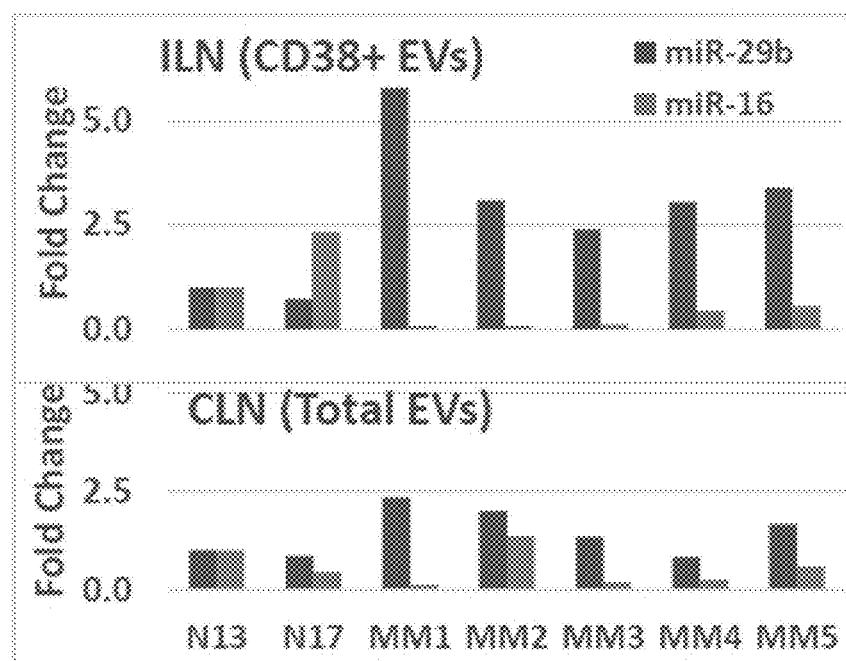
FIG. 7B is Comparison of signals for MM patient and healthy donor plasma normalized by healthy donor N13 conducted by immune-lipoplex nanoparticle (ILN) biochips with CD38+ EVs and CLN biochips with total EVs.

Example 8—Performance of CLN-Ohi-MB in CLN/ILN Biochips for Multiple Myeloma (MM) and Chronic Lymphocytic Leukemia (CLL) Diagnosis In the ILN biochip assay, antibodies are tethered on the chip surface to capture EVs rich in specific surface receptor. Cationic lipoplex nanoparticles containing RNA-specific molecular beacons are than applied to identify specific RNA targets in the captured EVs. This unique technology allows us to sort and probe individual EVs with both RNA and membrane protein targets. In FIGS. 7A and 7B, we demonstrated ILN mediated capture of MM-specific (CD38 positive) EVs, and then compared the ILN and CLN biochips for the detection of an up-regulated (miR-29b) and a down-regulated (miR-16) microRNA targets within the captured EVs. We sorted malignant MM cells (CD38$^{bright}$CD138+) and normal B cells (CD38$^{dim}$CD138-CD19+) from blood of MM patients by fluorescence activated cell sorting (FACS) and cultured the sorted cells overnight. Combining the separation assay with the molecular beacons encapsulated in tethered cationic lipoplex nanoparticles on our CLN biochip, we demonstrated that the expressions of two miRNA targets in EVs can be detected as shown in FIG. 7A, documenting that MM cells secreted more CD38+ EVs with up-regulated miR-29b (>5 fold) and 2-fold less miR-16 expression compared to the CD38$^{dim}$CD138-CD19+ normal cells from the same MM patient. Of note, miR-16 has been previously reported to be downregulated in MM patients compared to healthy donors. FIG. 7B shows that the ILN biochip with CLN-Ohi-MB can clearly distinguish MM patients from healthy donors by miR-29b and miR-16 expression in captured CD38+ EVs from 20 µL plasma samples. In comparison, the EV miR-29b and miR-16 expression based diagnosis performance using the CLN biochip with the same CLN-Ohi-MB is not as efficient because cationic lipoplex nanoparticles captured various EVs in plasma, instead of the MM specific CD38+ EV subgroup captured by the ILN biochip, without the tethered anti-CD38 mAb used in the ILN biochips.

Figure 7C:
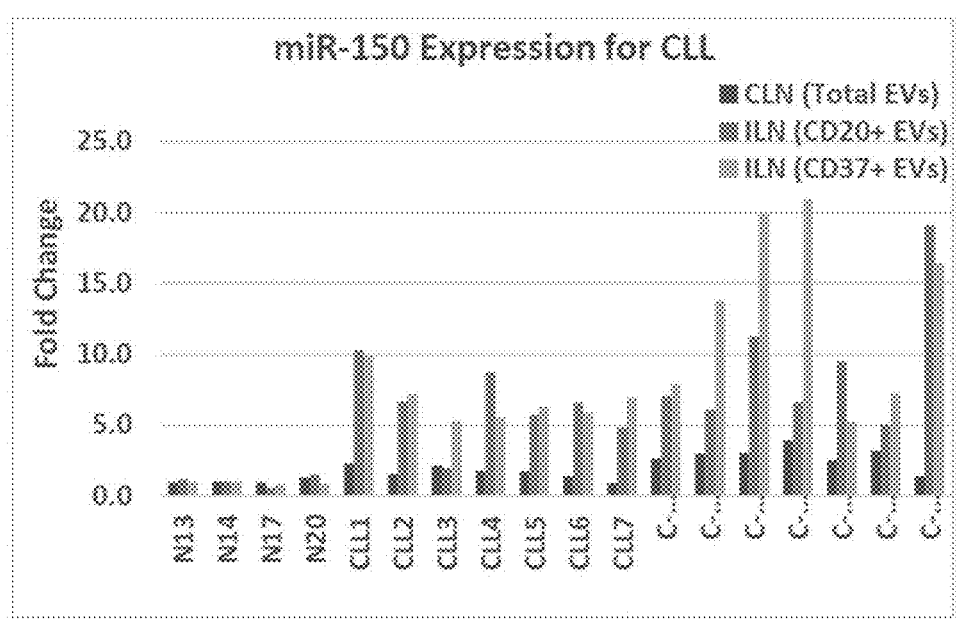
FIG. 7C is Comparison of EV miR-150 expression for CLL patient plasma (CLL) and their cancer cell culture media (C-MED) by healthy donor N14 conducted by ILN biochips with CD20+ and CD37+ EVs and CLN biochips with total EVs.

A similar performance for chronic lymphocytic leukemia (CLL) patients is shown in FIG. 7C where ILN biochips tethered with either CD20 or CD37 mAb are able to distinguish CLL patients from healthy donors with miR-150 expression detected by CLN-Ohi-MB in captured EV subgroups from 20 µL plasma samples. The miR-150 expression has been shown to be up-regulated in CLL, and CD20 and CD37 are known to be up-regulated in CLL cells too. For more efficient detection, antibody against known EV surface markers can be used in a microfluidic based ILN biochip to further enrich EV groups into more homogeneous sub-populations. Eventually, we can capture the EVs in ILN microfluidic chips coated with antibodies against markers of interest (e.g. anti-tetraspanin antibodies, anti-CD63, anti-CD9, anti-CD81, transferrin, folate, anti-EGFR, anti-integrand, etc.).

Figure 8A:
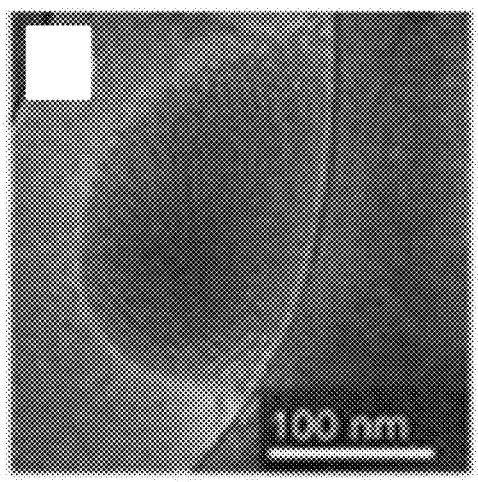
FIG. 8A is SV morphology by cryo-TEM micrograph.

Example 9—Design of a Universal Standard Vesicle (SV) as a Standard for Chip-to-Chip, Analyzer-to-Analyzer and Lab-to-Lab Calibration and Normalization for CLN/ILN Biochip Assays It is essential to have SV nanoparticles that can serve as a consistent model material and standard for CLN/ILN biochips, analyzers and other EV detection technologies for different users. We have designed lipopolyplex nanoparticles made of anionic lipids to serve as SVs. A typical phospholipids formulation includes 1,2-dioleoyl-sn-glycero-3-phosphoethanolamine (DOPE) (49%), linoleic acid (LA) (49%) and 1,2-Dimyristoyl-sn-glycerol methoxypolyethylene glycol (DMG-PEG) (2%) and the formed SV reveals a structure of cubosomes consisting of numerous inter-connected small cubic bilayer structures which allow encapsulation of a large amount of biomolecules as shown in FIG. 8A. Although cubosomes have different morphology from EVs, they are much more repeatable and stable, and can be lyophilized to form dry powder with consistent quality and long-term storage stability, essential for an internal standard. Since a target RNA in real EVs has a small copy number along with other RNAs, we only need to add a very small amount of target RNA oligo in the SV to mimic EV RNA contents. As an example, we prepared SVs with 1%, 2% and 4% concentration of single strand miR-21 mixed with a low-cost oligo-DNA (ODN) as scramble. These SVs were further diluted to 1%, 2%, 5%, 10%, 20% and 40% occupancy by blending with scramble SVs consisting of 100% scramble ODN since many real EVs do not contain any target RNAs. By preparing a series of solutions with different concentrations of SVs containing a target RNA oligo, the modified total fluorescence intensity (MFI) can be correlated to the known RNA oligo concentration determined by qRT-PCR to establish a calibration curve for analytical quantification.

Figure 8B:
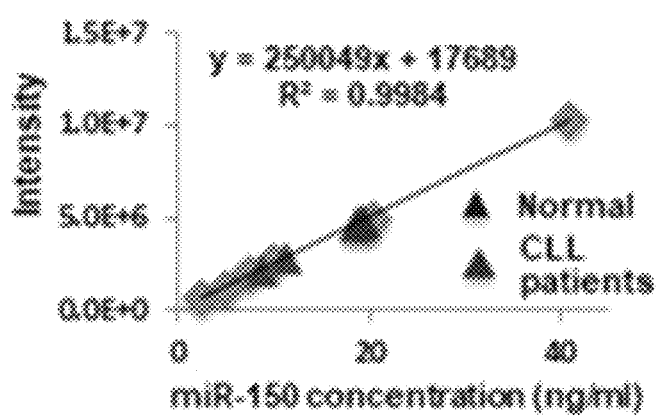
FIG. 8B is Calibration curves for SV blends, normal donors and CLL patients.
Figure 8C:
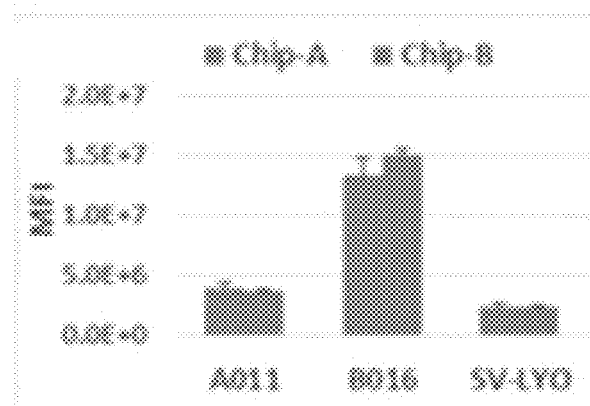
FIG. 8C is Liver cancer diagnosis calibrated by SVs.

FIG. 8B shows an example where SVs containing 1% miR-150_oligo at concentrations ranging from 1 to 40 ng/mL were detected using CLN-TIRF biochip assay and qRT-PCR with normal donor and Chronic Lymphocytic Leukemia (CLL) patient samples. A very good linear relationship was observed. FIG. 8C shows that these SV nanoparticles can be synthesized with consistent batch-to-batch quality for comparison with patient samples and can be stored in the powder form for a long shelf-life after lyophilization. We can replace scramble ODN by various RNA oligos in the SVs such that a universal SV may be synthesized to serve as a standard for hundreds of RNA targets in CLN/ILN biochip assay.

Example 10—Design of CLN-Oh-MB for MicroRNA Single-Point Edition Detection

Figure 9A:
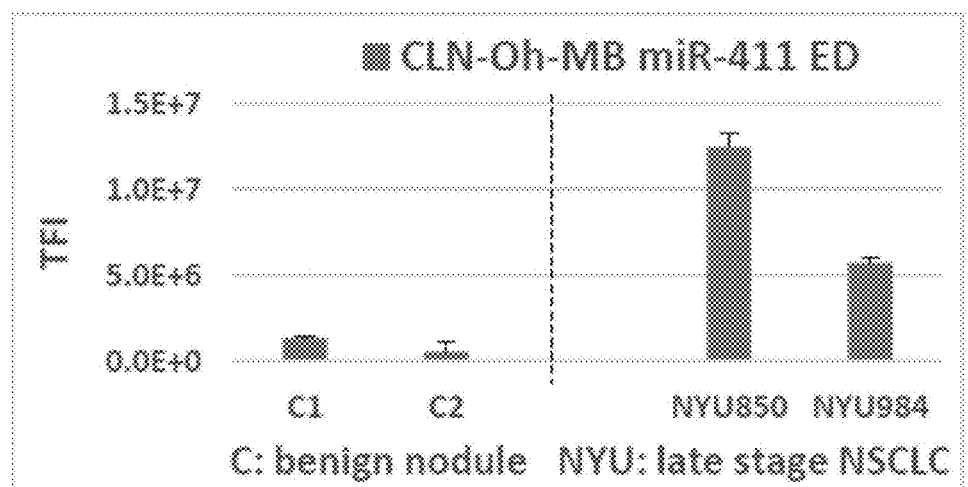
FIGS. 9A and 9B are The total fluorescence intensity (TFI) bar chart of miR-411 microRNA edition and representative TIRF fluorescence images confirming an increase of the fluorescence signal of non-small cell lung carcinoma (NSCLC) patient samples (NYU-850 and NYU-984) from New York University (NYU) comparing to patients (C1 and C2) with benign nodules.
Figure 9B:
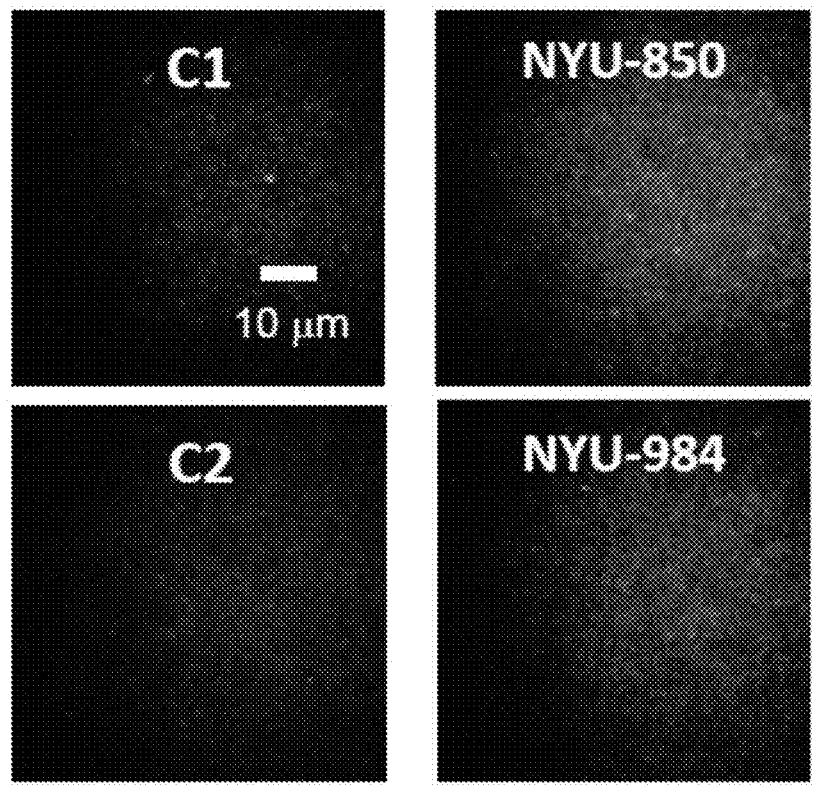

The CLN-Oh-MB can also be developed for microRNA single-point edition detection in early cancer diagnosis. The LNA nucleotides were also introduced into microRNA based CLN-Oh-MBs. The design of CLN-Oh-MBs used in this example for targeting miR-411 microRNA edition is shown in Table 1. The squared bases indicate the LNA nucleotides. The total fluorescence intensity (TFI) bar chart and representative TIRF fluorescence images confirmed an increase of the fluorescence signal of non-small cell lung carcinoma (NSCLC) patient samples (NYU-850 and NYU-984) from New York University (NYU) comparing to patients (C1 and C2) with benign nodules as shown in FIGS. 9A and 9B, respectively. Even though the patient number from NYU was small, the miR-411 edition detection was well recognized by using the CLN-Oh-MB with high specificity.

It should be emphasized that the above-described examples of the present disclosure are merely possible examples of implementations, and are merely set forth for a clear understanding of the principles of the disclosure. Many variations and modifications may be made to the above-described examples and embodiments, too. All such modifications and variations are intended to be included herein within the scope of this disclosure and protected by the following claims.

What is claimed is:

1. A method of detecting the presence of a target DNA, a mRNA, or a microRNA, in a subject, comprising:
   a) providing a liquid sample comprising cells, circulating tumor cells (CTCs), or extracellular vesicles (EVs);
   b) contacting the cells, circulating tumor cells (CTCs), or extracellular vesicles (EVs) with a cationic lipoplex nanoparticle, wherein the cationic lipoplex nanoparticle comprises a nucleic acid probe, wherein the nucleic acid probe comprises at least one stem, at least one loop, an overhang section, and at least one fluorescent dye, and wherein the nucleic acid probe comprises a nucleic acid sequence selected from the group consisting of SEQ ID No 2, SEQ ID No 4, SEQ ID No 5, SEQ ID No 6, SEQ ID No 7, SEQ ID No 9, SEQ ID No 11, SEQ ID No 12, and SEQ ID No 13;
   c) allowing the nucleic acid probe to hybridize to the target DNA, the mRNA, or the microRNA; and
   d) measuring a fluorescent signal to detect the target DNA, the mRNA, or the microRNA.

2. The method of claim 1, further comprising using SEQ ID No 4, SEQ ID No 5, or SEQ ID No 6 to detect one or more KRAS mutations.

3. The method of claim 1, further comprising using SEQ ID No 7 or SEQ ID No 9 to detect one or more EGFR mutations.

4. The method of claim 1, further comprising using SEQ ID No 11 or SEQ ID No 12 to detect an EML4-ALK fusion.

5. The method of claim 1, wherein the fluorescent dye comprises FAM, Cy3, or Cy5 at one end of the nucleic acid probe.

6. The method of claim 1, wherein the cells, circulating tumor cells (CTCs), or extracellular vesicles (EVs) are captured on a surface of a biochip by specific antibodies.

7. The method of claim 6, wherein universal standard vesicle (SV) nanoparticles comprising more than 100 target oligonucleotides from mRNA targets and miRNA targets are added as a standard for the biochip.

8. The method of claim 1, wherein the measuring the fluorescent signal is conducted with a detector selected from the group consisting of: a total internal reflective fluorescence (TIRF) microscope, a fluorescence microscope, a plate reader, and a portable fluorescence detector.

9. The method of claim 1, wherein the mRNA comprises a KRAS mutation, an EGFR mutation, or an EML4-ALK fusion.

10. The method of claim 1, wherein the liquid sample comprises a body fluid sample.

11. The method of claim 1, wherein the nucleic acid probe comprises DNA.

12. The method of claim 1, wherein the nucleic acid probe further comprises a quencher.

13. The method of claim 1, wherein the liquid sample comprises a blood sample, a serum sample, a plasma sample, a urine sample, a sputum sample, or a saliva sample from the subject.

* * * * *